United States Patent
Brain (12)

(10) Patent No.: US 9,675,772 B2
(45) Date of Patent: Jun. 13, 2017

(54) ARTIFICIAL AIRWAY DEVICE

(75) Inventor: Archibald Ian Jeremy Brain, Mahe (SC)

(73) Assignee: The Laryngeal Mask Company Limited, Victoria, Mahe (SC)

(*) Notice: Subject to any disclaimer, the term of this patent is extended or adjusted under 35 U.S.C. 154(b) by 547 days.

(21) Appl. No.: 13/879,377

(22) PCT Filed: Oct. 6, 2011

(86) PCT No.: PCT/GB2011/001453
§ 371 (c)(1),
(2), (4) Date: Jun. 24, 2013

(87) PCT Pub. No.: WO2012/049448
PCT Pub. Date: Apr. 19, 2012

(65) Prior Publication Data
US 2013/0269689 A1    Oct. 17, 2013

(30) Foreign Application Priority Data

Oct. 15, 2010  (GB) .................................. 1017453.0
Sep. 7, 2011   (GB) .................................. 1115156.4

(51) Int. Cl.
*A61M 16/00*    (2006.01)
*A61M 16/04*    (2006.01)

(52) U.S. Cl.
CPC .... *A61M 16/0463* (2013.01); *A61M 16/0057* (2013.01); *A61M 16/04* (2013.01);
(Continued)

(58) Field of Classification Search
CPC .............. A61M 16/04; A61M 16/0409; A61M 16/0415; A61M 16/042; A61M 16/0429;
(Continued)

(56) References Cited

U.S. PATENT DOCUMENTS

| 2,099,127 A | 11/1937 | Leech |
| 2,839,788 A | 6/1958 | Dembiak |

(Continued)

FOREIGN PATENT DOCUMENTS

| AU | 647437 | 6/1991 |
| CA | 2067782 | 11/1989 |

(Continued)

OTHER PUBLICATIONS

International Search Report for PCT/GB2006/001913, mailed Aug. 28, 2006.

(Continued)

*Primary Examiner* — Steven Douglas
(74) *Attorney, Agent, or Firm* — Knobbe, Martens, Olson & Bear, LLP

(57) ABSTRACT

An artificial airway device to facilitate lung ventilation of a patient, having an airway tube, a gastric drain tube and a mask at one end of the airway tube, the mask including a backplate and having a peripheral formation capable of forming a seal around the circumference of the laryngeal inlet, the peripheral formation surrounding a hollow interior space or lumen of the mask and the airway tube opening into the lumen of the mask, wherein the mask includes an atrium for passage to the gastric drain tube of gastric matter leaving the esophagus is disclosed.

11 Claims, 15 Drawing Sheets

(52) U.S. Cl.
CPC .... *A61M 16/0409* (2014.02); *A61M 16/0415* (2014.02); *A61M 16/0434* (2013.01); *A61M 16/0488* (2013.01)

(58) Field of Classification Search
CPC .......... A61M 16/0463; A61M 16/0434; A61M 16/0057; A61M 16/0488
USPC ...................................... 128/207.14–207.17
See application file for complete search history.

(56) References Cited

U.S. PATENT DOCUMENTS

| | | |
|---|---|---|
| 2,862,498 A | 12/1958 | Weekes |
| 3,529,596 A | 9/1970 | Garner |
| 3,554,673 A | 1/1971 | Schwartz et al. |
| 3,576,187 A | 4/1971 | Oddera |
| 3,683,908 A | 8/1972 | Michael et al. |
| 3,794,036 A | 2/1974 | Carroll |
| 3,931,822 A | 1/1976 | Marici |
| 3,948,273 A | 4/1976 | Sanders |
| 4,056,104 A | 11/1977 | Jaffe |
| 4,067,329 A | 1/1978 | Winicki et al. |
| 4,104,357 A | 8/1978 | Blair |
| 4,116,201 A | 9/1978 | Shah |
| 4,134,407 A | 1/1979 | Elam |
| 4,159,722 A | 7/1979 | Walker |
| 4,166,467 A | 9/1979 | Abramson |
| 4,178,938 A | 12/1979 | Au et al. |
| 4,178,940 A | 12/1979 | Au et al. |
| 4,231,365 A | 11/1980 | Scarberry |
| 4,256,099 A | 3/1981 | Dryden |
| 4,285,340 A | 8/1981 | Gezari et al. |
| 4,351,330 A * | 9/1982 | Scarberry ................ 128/207.15 |
| 4,363,320 A | 12/1982 | Kossove |
| 4,446,864 A | 5/1984 | Watson et al. |
| 4,471,775 A | 9/1984 | Clair et al. |
| 4,501,273 A | 2/1985 | McGinnis |
| 4,509,514 A | 4/1985 | Brain et al. |
| 4,510,273 A | 4/1985 | Miura et al. |
| 4,526,196 A | 7/1985 | Pistillo |
| 4,553,540 A | 11/1985 | Straith |
| 4,583,917 A | 4/1986 | Shah |
| 4,630,606 A | 12/1986 | Weerda et al. |
| 4,689,041 A | 8/1987 | Corday et al. |
| 4,700,700 A | 10/1987 | Eliachar |
| 4,770,170 A | 9/1988 | Sato et al. |
| 4,793,327 A | 12/1988 | Frankel |
| 4,798,597 A | 1/1989 | Vaillancourt |
| 4,825,862 A | 5/1989 | Sato et al. |
| 4,832,020 A | 5/1989 | Auqustine |
| 4,850,349 A | 7/1989 | Farahany |
| 4,856,510 A | 8/1989 | Kowalewski et al. |
| 4,872,483 A | 10/1989 | Shah |
| 4,896,667 A | 1/1990 | Magnusson et al. |
| 4,924,862 A | 5/1990 | Levinson |
| 4,953,547 A | 9/1990 | Poole, Jr. |
| 4,972,963 A | 11/1990 | Guarriello et al. |
| 4,981,470 A | 1/1991 | Bombeck, IV |
| 4,995,388 A | 2/1991 | Brain et al. |
| 5,038,766 A | 8/1991 | Parker |
| 5,042,469 A | 8/1991 | Augustine |
| 5,042,476 A | 8/1991 | Smith |
| 5,060,647 A | 10/1991 | Alessi |
| 5,067,496 A | 11/1991 | Eisele |
| 5,113,875 A | 5/1992 | Bennett |
| 5,174,283 A | 12/1992 | Parker |
| 5,203,320 A | 4/1993 | Augustine |
| 5,218,970 A | 6/1993 | Turnbull et al. |
| 5,235,973 A | 8/1993 | Levinson |
| 5,241,325 A | 8/1993 | Nguyen et al. |
| 5,241,956 A | 9/1993 | Brain et al. |
| 5,249,571 A | 10/1993 | Brain et al. |
| 5,273,537 A | 12/1993 | Haskvitz et al. |
| 5,277,178 A | 1/1994 | DinQiey et al. |
| 5,282,464 A | 2/1994 | Brain et al. |
| 5,297,547 A | 3/1994 | Brain et al. |
| 5,303,697 A | 4/1994 | Brain et al. |
| 5,305,743 A | 4/1994 | Brain |
| 5,311,861 A | 5/1994 | Miller et al. |
| 5,318,017 A | 6/1994 | Ellison |
| 5,331,967 A | 7/1994 | Akerson et al. |
| 5,339,805 A | 8/1994 | Parker |
| 5,339,808 A | 8/1994 | Don Michael |
| 5,355,879 A | 10/1994 | Brain et al. |
| 5,361,753 A | 11/1994 | Pothmann et al. |
| 5,391,248 A | 2/1995 | Brain et al. |
| 5,400,771 A | 3/1995 | Pirak et al. |
| 5,421,325 A | 6/1995 | Cinberg et al. |
| 5,438,982 A | 8/1995 | Macintyre |
| 5,443,063 A | 8/1995 | Greenberg |
| 5,452,715 A | 9/1995 | Boussignac et al. |
| 5,459,700 A | 10/1995 | Jacobs |
| 5,487,383 A | 1/1996 | Levinson |
| 5,529,582 A | 6/1996 | Fukuhara et al. |
| 5,546,935 A | 8/1996 | Champeau |
| 5,546,936 A | 8/1996 | Virag et al. |
| 5,551,420 A | 9/1996 | Lurie et al. |
| 5,554,673 A | 9/1996 | Shah |
| 5,569,219 A | 10/1996 | Hakki et al. |
| 5,577,693 A | 11/1996 | Corn |
| 5,582,167 A | 12/1996 | Joseph |
| 5,584,290 A | 12/1996 | Brain et al. |
| 5,590,643 A | 1/1997 | Flam |
| 5,599,301 A | 2/1997 | Jacobs et al. |
| 5,623,921 A | 4/1997 | Kinsinger et al. |
| 5,626,151 A | 5/1997 | Linden |
| 5,632,271 A | 5/1997 | Brain et al. |
| RE35,531 E | 6/1997 | Callaghan et al. |
| 5,653,229 A | 8/1997 | Greenberg |
| 5,655,528 A | 8/1997 | Paqan et al. |
| 5,682,880 A | 11/1997 | Brain et al. |
| 5,692,498 A | 12/1997 | Lurie et al. |
| 5,694,929 A | 12/1997 | Christopher |
| 5,711,293 A | 1/1998 | Brain et al. |
| 5,738,094 A | 4/1998 | Hottman |
| 5,743,254 A | 4/1998 | Parker |
| 5,743,258 A | 4/1998 | Sato et al. |
| 5,746,202 A | 5/1998 | Paqan et al. |
| 5,771,889 A | 6/1998 | Pagan et al. |
| 5,778,872 A | 7/1998 | Fukunaga et al. |
| 5,791,341 A | 8/1998 | Bullard |
| 5,794,617 A | 8/1998 | Brunell et al. |
| 5,816,240 A | 10/1998 | Komesaroff |
| 5,819,723 A | 10/1998 | Joseph |
| 5,832,916 A | 11/1998 | Lundberg et al. |
| 5,850,832 A | 12/1998 | Chu |
| 5,855,203 A | 1/1999 | Matter |
| 5,856,510 A | 1/1999 | Meng et al. |
| 5,860,418 A | 1/1999 | Lundberg et al. |
| 5,862,801 A | 1/1999 | Wells |
| 5,865,176 A | 2/1999 | O'Neil et al. |
| 5,878,745 A | 3/1999 | Brain et al. |
| 5,881,726 A | 3/1999 | Neame |
| 5,893,891 A | 4/1999 | Zahedi et al. |
| 5,896,858 A | 4/1999 | Brain |
| 5,915,383 A | 6/1999 | Pagan |
| 5,921,239 A | 7/1999 | McCall et al. |
| 5,924,862 A | 7/1999 | White |
| 5,937,860 A | 8/1999 | Cook |
| 5,957,133 A | 9/1999 | Hart |
| 5,976,075 A | 11/1999 | Beane et al. |
| 5,979,445 A | 11/1999 | Neame et al. |
| 5,983,891 A | 11/1999 | Fukunaga |
| 5,983,896 A | 11/1999 | Fukunaqa et al. |
| 5,983,897 A | 11/1999 | Pagan |
| 5,988,167 A | 11/1999 | Kamen |
| 5,996,582 A | 12/1999 | Turnbull |
| 6,003,510 A | 12/1999 | Anunta |
| 6,003,511 A | 12/1999 | Fukunaga et al. |
| 6,003,514 A | 12/1999 | Pagan |
| 6,012,452 A | 1/2000 | Pagan |
| 6,021,779 A | 2/2000 | Paqan |
| 6,050,264 A | 4/2000 | Greenfield |
| 6,062,219 A | 5/2000 | Lurie et al. |

(56) References Cited

U.S. PATENT DOCUMENTS

| | | |
|---|---|---|
| 6,070,581 A | 6/2000 | Augustine et al. |
| 6,079,409 A | 6/2000 | Brain et al. |
| D429,811 S | 8/2000 | Bermudez et al. |
| 6,095,144 A | 8/2000 | Pagan |
| 6,098,621 A | 8/2000 | Esnouf et al. |
| 6,110,143 A | 8/2000 | Kamen |
| 6,116,243 A | 9/2000 | Pagan |
| 6,119,695 A | 9/2000 | Augustine et al. |
| 6,131,571 A | 10/2000 | Lamootang et al. |
| 6,149,603 A | 11/2000 | Parker |
| 6,155,257 A | 12/2000 | Lurie et al. |
| 6,213,120 B1 | 4/2001 | Block et al. |
| 6,224,562 B1 | 5/2001 | Lurie et al. |
| 6,234,985 B1 | 5/2001 | Lurie et al. |
| 6,240,922 B1 | 6/2001 | Pagan |
| 6,251,093 B1 | 6/2001 | Valley et al. |
| 6,269,813 B1 | 8/2001 | Fitzgerald et al. |
| 6,315,739 B1 | 11/2001 | Merilainen et al. |
| 6,338,343 B1 | 1/2002 | Augustine et al. |
| 6,352,077 B1 | 3/2002 | Shah |
| 6,386,199 B1 | 5/2002 | Alfery |
| 6,390,093 B1 | 5/2002 | Mongeon |
| 6,422,239 B1 | 7/2002 | Cook |
| 6,427,686 B2 | 8/2002 | Augustine et al. |
| 6,439,232 B1 | 8/2002 | Brain |
| 6,450,164 B1 | 9/2002 | Banner et al. |
| 6,508,250 B1 | 1/2003 | Esnouf |
| 6,546,931 B2 | 4/2003 | Lin et al. |
| 6,631,720 B1 | 10/2003 | Brain et al. |
| 6,647,984 B1 | 11/2003 | O'Dea et al. |
| 6,651,666 B1 | 11/2003 | Owens |
| 6,705,318 B1 | 3/2004 | Brain |
| 6,766,801 B1 | 7/2004 | Wright |
| 6,955,645 B1 | 10/2005 | Zeitels |
| 7,004,169 B2 | 2/2006 | Brain et al. |
| 7,040,322 B2 | 5/2006 | Fortuna et al. |
| 7,051,096 B1 | 5/2006 | Krawiec et al. |
| 7,051,736 B2 | 5/2006 | Banner et al. |
| 7,096,868 B2 | 8/2006 | Tateo et al. |
| 7,097,802 B2 | 8/2006 | Brain et al. |
| 7,128,071 B2 | 10/2006 | Brain et al. |
| 7,134,431 B2 | 11/2006 | Brain et al. |
| 7,156,100 B1 | 1/2007 | Brain et al. |
| 7,159,589 B2 | 1/2007 | Brain |
| RE39,938 E | 12/2007 | Brain |
| 7,383,736 B2 | 6/2008 | Esnouf |
| 7,694,682 B2 | 4/2010 | Petersen et al. |
| 7,997,274 B2 | 8/2011 | Baska |
| 8,033,176 B2 | 10/2011 | Esnouf |
| 8,413,658 B2 | 4/2013 | Williams |
| 2003/0000534 A1 | 1/2003 | Alfery |
| 2003/0037790 A1 | 2/2003 | Brain |
| 2003/0051734 A1 | 3/2003 | Brain |
| 2003/0101998 A1 | 6/2003 | Zecca et al. |
| 2003/0131845 A1 | 7/2003 | Lin |
| 2003/0168062 A1 | 9/2003 | Blythe et al. |
| 2003/0172925 A1 | 9/2003 | Zecca et al. |
| 2003/0172935 A1 | 9/2003 | Miller |
| 2004/0020491 A1 | 2/2004 | Fortuna |
| 2004/0089307 A1 | 5/2004 | Brain |
| 2005/0066975 A1 | 3/2005 | Brain |
| 2005/0081861 A1 | 4/2005 | Nasir |
| 2005/0090712 A1 | 4/2005 | Cubb |
| 2005/0133037 A1 | 6/2005 | Russell |
| 2005/0139220 A1 | 6/2005 | Christopher |
| 2005/0178388 A1 | 8/2005 | Kuo |
| 2005/0199244 A1 | 9/2005 | Tateo et al. |
| 2005/0274383 A1 | 12/2005 | Brain |
| 2006/0124132 A1 | 6/2006 | Brain |
| 2006/0180156 A1* | 8/2006 | Baska .................... 128/207.15 |
| 2006/0201516 A1 | 9/2006 | Petersen et al. |
| 2006/0254596 A1 | 11/2006 | Brain |
| 2007/0089754 A1 | 4/2007 | Jones |
| 2007/0240722 A1 | 10/2007 | Kessler |
| 2008/0041392 A1 | 2/2008 | Cook |
| 2008/0142017 A1 | 6/2008 | Brain |
| 2008/0276936 A1 | 11/2008 | Cook |
| 2008/0308109 A1 | 12/2008 | Brain |
| 2009/0090356 A1 | 4/2009 | Cook |
| 2009/0133701 A1 | 5/2009 | Brain |
| 2009/0139524 A1 | 6/2009 | Esnouf |
| 2009/0145438 A1 | 6/2009 | Brain |
| 2010/0059061 A1 | 3/2010 | Brain |
| 2010/0089393 A1 | 4/2010 | Brain |
| 2010/0211140 A1 | 8/2010 | Barbut et al. |
| 2010/0242957 A1 | 9/2010 | Fortuna |
| 2011/0023890 A1 | 2/2011 | Baska |
| 2011/0220117 A1 | 9/2011 | Dubach |
| 2012/0085351 A1 | 4/2012 | Brain |
| 2012/0090609 A1 | 4/2012 | Dubach |
| 2012/0145161 A1 | 6/2012 | Brain |
| 2012/0174929 A1 | 7/2012 | Esnouf |
| 2012/0186510 A1 | 7/2012 | Esnouf |
| 2014/0034060 A1 | 2/2014 | Esnouf et al. |
| 2015/0209538 A1 | 7/2015 | Hansen |

FOREIGN PATENT DOCUMENTS

| | | |
|---|---|---|
| CA | 2141167 | 1/1994 |
| CA | 2012750 | 8/1999 |
| DE | 4447186 | 7/1996 |
| DE | 10042172 A1 | 4/2001 |
| EP | 0294200 A2 | 12/1988 |
| EP | 0294200 B1 | 12/1988 |
| EP | 0389272 A2 | 9/1990 |
| EP | 0402872 A1 | 12/1990 |
| EP | 0580385 A1 | 1/1994 |
| EP | 0712638 A1 | 5/1996 |
| EP | 0732116 A2 | 9/1996 |
| EP | 0796631 A2 | 9/1997 |
| EP | 0842672 A2 | 5/1998 |
| EP | 0845276 A2 | 6/1998 |
| EP | 0865798 A2 | 9/1998 |
| EP | 0922465 A2 | 6/1999 |
| EP | 0935971 A2 | 8/1999 |
| EP | 1119386 B1 | 8/2001 |
| EP | 1125595 A1 | 8/2001 |
| EP | 1 938 855 | 7/2008 |
| EP | 2 044 969 | 4/2009 |
| GB | 1529190 A | 10/1978 |
| GB | 2111394 A | 7/1983 |
| GB | 2205499 A | 12/1988 |
| GB | 2 298 580 | 9/1996 |
| GB | 2298797 A | 9/1996 |
| GB | 2317342 A | 3/1998 |
| GB | 2317830 A | 4/1998 |
| GB | 2318735 A | 5/1998 |
| GB | 2319478 A | 5/1998 |
| GB | 2321854 A | 8/1998 |
| GB | 2323289 A | 9/1998 |
| GB | 2323290 A | 9/1998 |
| GB | 2323291 A | 9/1998 |
| GB | 2323292 A | 9/1998 |
| GB | 2324737 A | 11/1998 |
| GB | 2334215 A | 8/1999 |
| GB | 2359996 A | 9/2001 |
| GB | 2371990 A | 8/2002 |
| GB | 2 404 863 | 2/2005 |
| GB | 2405588 A | 3/2005 |
| GB | 2 444 779 | 6/2008 |
| GB | 2 465 453 | 5/2010 |
| JP | 03039169 A | 2/1991 |
| JP | 10118182 A | 5/1998 |
| JP | 10216233 A | 8/1998 |
| JP | 10263086 A | 10/1998 |
| JP | 10277156 A | 10/1998 |
| JP | 10314308 A | 12/1998 |
| JP | 10323391 A | 12/1998 |
| JP | 10328303 A | 12/1998 |
| JP | 11128349 A | 5/1999 |
| JP | 11192304 A | 7/1999 |
| JP | 11206885 A | 8/1999 |
| JP | 2000152995 A | 6/2000 |
| JP | 2003528701 A | 9/2003 |

(56) References Cited

FOREIGN PATENT DOCUMENTS

| WO | WO9103207 A1 | 3/1991 |
|----|----|----|
| WO | WO9107201 A1 | 5/1991 |
| WO | WO9112845 A1 | 9/1991 |
| WO | WO9213587 A1 | 8/1992 |
| WO | WO 94/02191 | 2/1994 |
| WO | WO9402191 A1 | 2/1994 |
| WO | WO9533506 A1 | 12/1995 |
| WO | WO9712640 A1 | 4/1997 |
| WO | WO9712641 A1 | 4/1997 |
| WO | WO9816273 A1 | 4/1998 |
| WO | WO9850096 | 11/1998 |
| WO | WO9906093 A1 | 2/1999 |
| WO | WO 99/27840 | 6/1999 |
| WO | WO0009189 A1 | 2/2000 |
| WO | WO0022985 A1 | 4/2000 |
| WO | WO0023135 A1 | 4/2000 |
| WO | WO0061212 A1 | 10/2000 |
| WO | WO0124860 | 4/2001 |
| WO | WO0174431 A2 | 10/2001 |
| WO | WO0232490 A2 | 4/2002 |
| WO | WO 2004/016308 | 2/2004 |
| WO | WO2004030527 A1 | 4/2004 |
| WO | WO 2004/089453 | 10/2004 |
| WO | WO 2005/011784 | 2/2005 |
| WO | WO2005011784 A1 | 2/2005 |
| WO | WO2005023350 A1 | 3/2005 |
| WO | WO 2005/046751 | 5/2005 |
| WO | WO2006026237 A1 | 3/2006 |
| WO | WO2006125989 A1 | 11/2006 |
| WO | WO 2007071429 | 10/2007 |
| WO | WO 2008/001724 | 1/2008 |
| WO | WO 2009/026628 | 3/2009 |
| WO | WO 2010/060227 | 6/2010 |
| WO | WO 2010/066001 | 6/2010 |
| WO | WO 2010060226 | 6/2010 |

OTHER PUBLICATIONS

M.O. Abdelatti; "A Cuff Pressure Controller for Tracheal Tubes and Laryngeal Mask Airways" Anaesthesia, 1999, 54, pp. 981-986 (1999 Blackwell Science Ltd).
Jonathan L. Benumo, M.D.; "Laryngeal Mask Airway and the ASA Difficult Airway Algorithm" Medical Intelligence Article; Anesthesiology, V 84, No. 3, Mar. 1996 (686-99).
Jonathan L. Benumo, M.D.; "Management of the Difficult Adult Airway" With Special Emphasis on Awake Tracheal Intubation; Anesthesiology V 75, No. 6: 1087-1110, 1991.
Bernhard, et al.; "Adjustment of Intracuff Pressure to Prevent Aspiration" ; Anesthesiology, vol. 50, No. 4, 363-366, Apr. 1979.
Bernhard, et al.; "Physical Characteristics of and Rates of Nitrous Oxide Diffusion into Tracheal Tube Cuffs" Anesthesiology, vol. 48, No. 6 Jun. 1978, 413-417.
A.I.J. Brain, et al.: "The Laryngeal Mask Airway" Anaesthesia, 1985, vol. 40, pp. 356-361.
A.I.J. Brain, et al.: "The Laryngeal Mask Airway—A Possible New Solution to Airway Problems in the Emergency Situation" Archives of Emergency Medicine, 1984, vol. 1, p. 229-232.
A.I.J. Brain; "The Laryngeal Mask—A New Concept in Airway Management" British Journal of Anaesthesia, 1983, vol. 55, p. 801-805.
A.I.J. Brain, et al.: "A New Laryngeal Mask Prototype" Anaesthesia, 1995, vol. 50, pp. 42-48.
A.I.J. Brain; "Three Cases of Difficult Intubation Overcome by the Laryngeal Mask Airway" ; Anaesthesia, 1985, vol. 40, pp. 353-355.
J. Brimacombe; "The Split Laryngeal Mask Airway" ; Royal Perth Hospital, Perth 6001 Western Australia; Correspondence p. 639.
P.M. Brodrick et al.; "The Laryngeal Mask Airway" ; Anaesthesia, 1989, vol. 44, pp. 238-241; The Association of Anaesthetists of Gt Britain and Ireland.
Burgard et al.; "The Effect of Laryngeal Mask Cuff Pressure on Postoperative Sore Throat Incidence" ; Journal of Clinical Anesthesia 8: 198-201, 1996 by Elsevier Science Inc.
Caplan, et al.; "Adverse Respiratory Events in Anesthesia: A Closed Claims Analysis"; Anesthesiology vol. 72, No. 5: 828-833, May 1990.
Donald E. Craven, MD; "Prevention of Hospital-Acquired Pneumonia: Meaning Effect in Ounces, Pounds, and Tons"; Annals of Internal Medicine, vol. 122, No. 3, Feb. 1, 1995, pp. 229-231.
"Cuff-Pressure-Control CDR 2000"; LogoMed, Klarenplatz 11, D-53578 Windhagen, pp. 1-4.
P.R.F. Davies et al.; "Laryngeal Mask Airway and Tracheal Tube Insertion by Unskilled Personnel"; The Lancet, vol. 336, p. 977-979.
DeMello et al.; "The Use of the Laryngeal Mask Airway in Primary Anaesthesia" Cambridge Military Hospital, Aldershot, Hants GU11 2AN; pp. 793-794.
Doyle et al.; "Intraoperative Awareness: A Continuing Clinical Problem"; Educational Synopses in Anesthesiology and Critical Care Medicine The Online Journal of Anesthesiology vol. 3 No. 6 Jun. 1996, pp. 1-8.
F. Engbers; "Practical Use of 'Diprifusor' Systems"; Anaesthesia, 1998, vol. 53, Supplement 1, pp. 28-34; Blackwell Science Ltd.
Eriksson et al.; "Functional Assessment of the Pharynx at Rest and During Swallowing in Partially Paralyzed Humans" Anesthesiology, vol. 87, No. 5, Nov. 1997, pp. 1035-1042.
J.B. Glen; "The Development of 'Diprifusor': A TCI System for Propofol" Anaesthesia, 1998, vol. 53, Supplement 1, pp. 13-21, Blackwell Science Ltd.
J.M. Gray et al.; "Development of the Technology for 'Diprifusor' TCI Systems"; Anaesthesia, 1998, vol. 53, Supplement 1, pp. 22-27, Blackwell Science Ltd.
M.L. Heath; "Endotracheal Intubation Through the Laryngeal Mask—Helpful When Laryngoscopy is Difficult or Dangerous"; European Journal of Anaesthesiology 1991, Supplement 4, pp. 41-45.
S. Hickey et al.; "Cardiovascular Response to Insertion of Brian's Laryngeal Mask"; Anaesthesia, 1990, vol. 45, pp. 629-633, The Association of Anaesthetists of Gt Britain and Ireland.
Inomata et al.; "Transient Bilateral Vocal Cord Paralysis after Insertion of a Laryngeal Mask Airway"; Anesthesiology, vol. 82, No. 3, Mar. 1995, pp. 787-788.
L. Jacobson et al.; "A Study of Intracuff Pressure Measurements, Trends and Behaviour in Patients During Prolonged Periods of Tracheal Intubation" British Journal of Anaesthesia (1981), vol. 53, pp. 97-101; Macmillan Publishers Ltd. 1981.
V. Kambic et al.; "Intubation Lesions of the Larynx"; British Journal of Anaesthesia (1978), vol. 50, pp. 587-590; Macmillan Journals Ltd. 1978.
A.Kapila et al.; "Intubating Laryngeal Mask Airway: A Preliminary Assessment of Performance"; British Journal of Anaesthesia 1995, vol. 75: pp. 228-229.
Carl-Eric Lindholm; "Prolonged Endotracheal Intubation" ; Iussu Societatis Anaesthesiologicae Scandinavica Edita Suppllementum XXXIII 1969 v. 33 pp. 29-46.
S. Majumder et al.; "Bilateral Lingual Nerve Injury Following the Use of the Laryngeal Mask Airway" ; Anaesthesia, 1998, vol. 53, pp. 184-186, 1998 Blackwell Science Ltd.
Todd Martin; "Patentability of Methods of Medical Treatment: A Comparative Study"; HeinOnLine—82 J. Pat. & Trademark Off. Soc'y 2000, pp. 381-423.
Merriam-Webster's Collegiate Dictionary Tenth Edition, Springfield, Mass, U.S.A. (Convex) p. 254 & (Saddle) p. 1029.
D.M. Miller; "A Pressure Regulator for the Cuff of a Tracheal Tube" Anaesthesia, 1992, vol. 47, pp. 594-596; 1992 The Association of Anaesthetists of Gt Britain and Ireland.
Muthuswamy et al.; "The Use of Fuzzy Integrals and Bispectral Analysis of the Electroencephalogram to Preddict Movement Under Anesthesia"; Ieee Transactions on Biomedical Engineering, vol. 46, No. 3, Mar. 1999, pp. 291-299.
K. Nagai et al.; "Unilateral Hypoglossal Nerve Paralysis Following the Use of the Laryngeal Mask Airway"; Anaesthesia, 1994, vol. 49, pp. 603-604; 1994 The Association of Anaesthetists of Gt Britain and Ireland.

(56) References Cited

OTHER PUBLICATIONS

Lars J. Kangas; "Neurometric Assessment of Adequacy of Intraoperative Anesthetic" Medical Technology Brief, Pacific Northwest National Laboratory, pp. 1-3.
Observations by a third party concerning the European Patent Application No. 99947765.6-2318, dated Jan. 18, 2005.
R.I. Patel et al.; "Tracheal Tube Cuff Pressure"; Anaesthesia, 1984, vol. 39, pp. 862-864; 1984 The Association of Anaesthetists of Gt Britain and Ireland.
Written Opinion of the International Searching Authority for Application No. PCT/GB2006/001913.
Pennant et al.; "Comparison of the Endotracheal Tube and Laryngeal Mask in Airway Management by Paramedical Personnel"; Dept of Anesthesiology, University of Texas Southwestern Medical School; Anesth Analg 1992, vol. 74, pp. 531-534.
Pippin et al.; "Long-Term Tracheal Intubation Practice in the United Kingdom"; Anaesthesia, 1983, vol. 38, pp. 791-795.
J.C. Raeder et al.; "Tracheal Tube Cuff Pressures" Anaesthesia, 1985, vol. 40, pp. 444-447; 1985 The Association of Anaesthetists of Gt Britain and Ireland.
Response to Complaint for matter No. 4b 0 440-05, *LMA Deutschland GmbH* vs. *Ambu (Deutschland) GmbH*, dated Feb. 10, 2006.
Rieger et al.; "Intracuff Pressures Do Not Predict Laryngopharyngeal Discomfort after Use of the Laryngeal Mask Airway"; Anesthesiology 1997, vol. 87, pp. 63-67; 1997 American Society of Anesthesiologists, Inc.
R D Seegobin et al.; "Endotracheal Cuff Pressure and Tracheal Mucosal Blood Flow: Endoscopic Study of Effects of Four Large Volume Cuffs"; British Medical Jornal, vol. 288, Mar. 31, 1984, pp. 965-968.
B.A. Willis et al.; "Tracheal Tube Cuff Pressure" Anaesthesia, 1988, vol. 43, pp. 312-314; The Asš ociation of Anaesthetists of Gt Britain and Ireland.
L. Worthington et al.; "Performance of Vaporizers in Circle Systems" British Journal of Anaesthesia 1995, vol. 75.
J. Michael Wynn, M.D.; "Tongue Cyanosis after Laryngeal Mask Airway Insertion" Anesthesiology, vol. 80, No. 6, Jun. 1994, p. 1403.
Brimacombe, Joseph R., "Laryngeal Mask Anesthesia" Second Edition, Saunders 2005.
"Anaesthetic and respiratory equipment—Supralaryngeal airways and connectors", International Standard Controlled, ISO 11712, ISO 2009.
Miller, Donald, "A Proposed Classification and Scoring System for Supraglottic Sealing Airways: A Brief Review", Anesth Analg 2004; 99:1553-9.
Benumof, Jonathan, "The Glottic Aperture Seal Airway. A New Ventilatory Device", Anesthesiology, V. 88, No. 5., May 1998, pp. 1219-1226.
McIntyre, John, "History of Anaesthesia" Oropharyngeal and nasopharyngeal airways: I (1880-1995), Can. J. Anaesth 1996, vol. 43, vol. 6, pp. 629-635.
Ishimura, et al., "Impossible Insertion of the Laryngeal Mask Airway and Oropharyngeal Axes", Anesthesiology, V. 83, No. 4., Oct. 1995, pp. 867-869.
Verghese, et al., "Clinical assessment of the single use laryngeal mask airway—the LMA-Unique", British Journal of Anaesthesia 1998; vol. 80: 677-679.

* cited by examiner

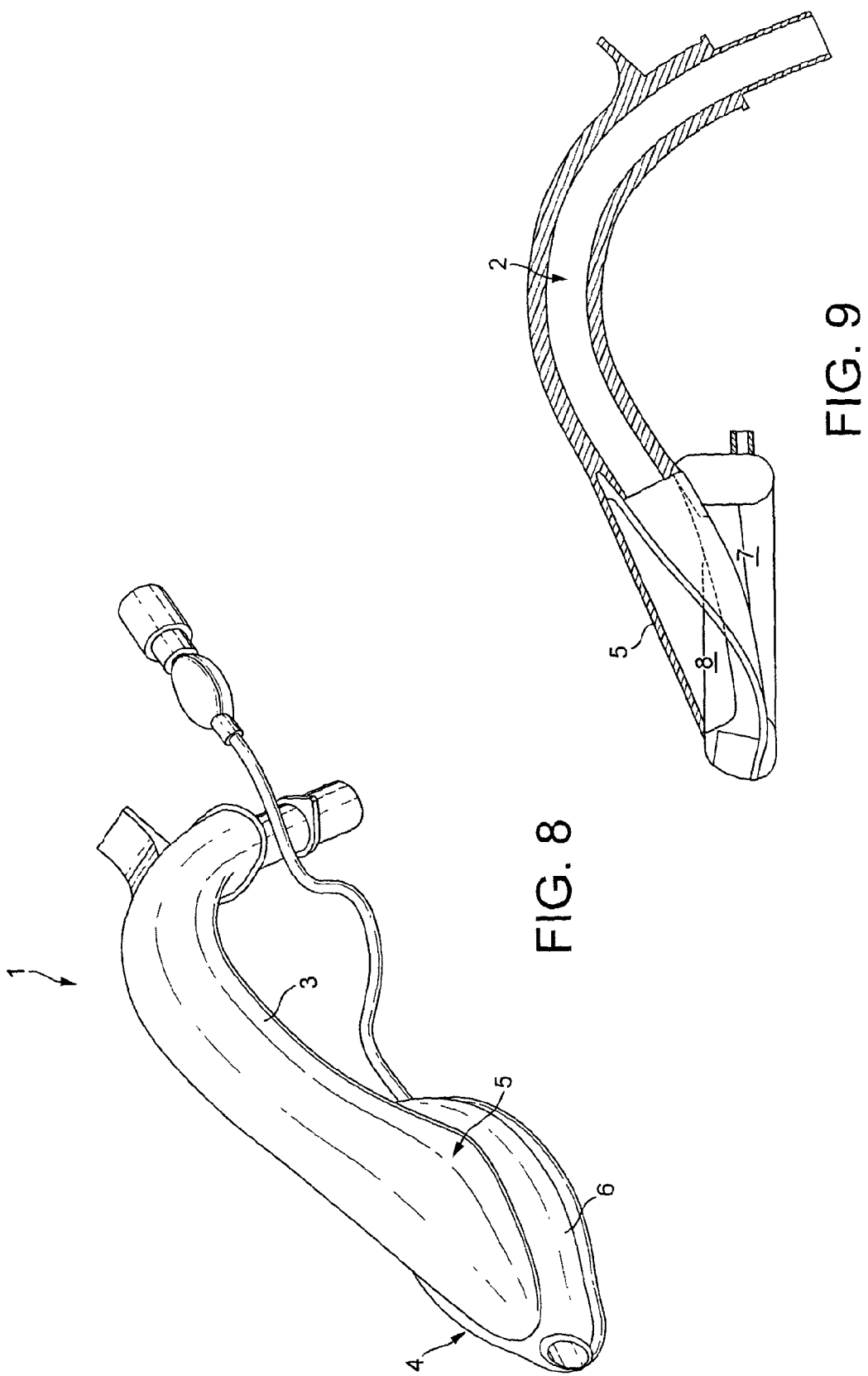

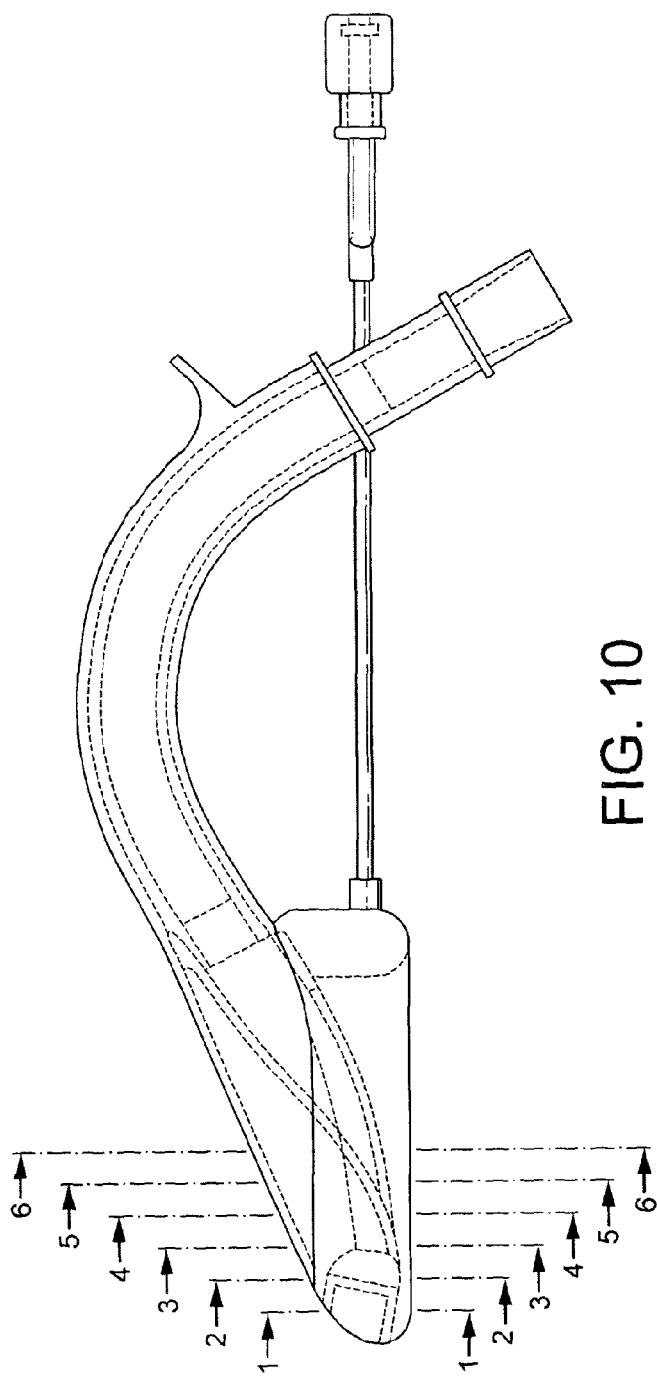

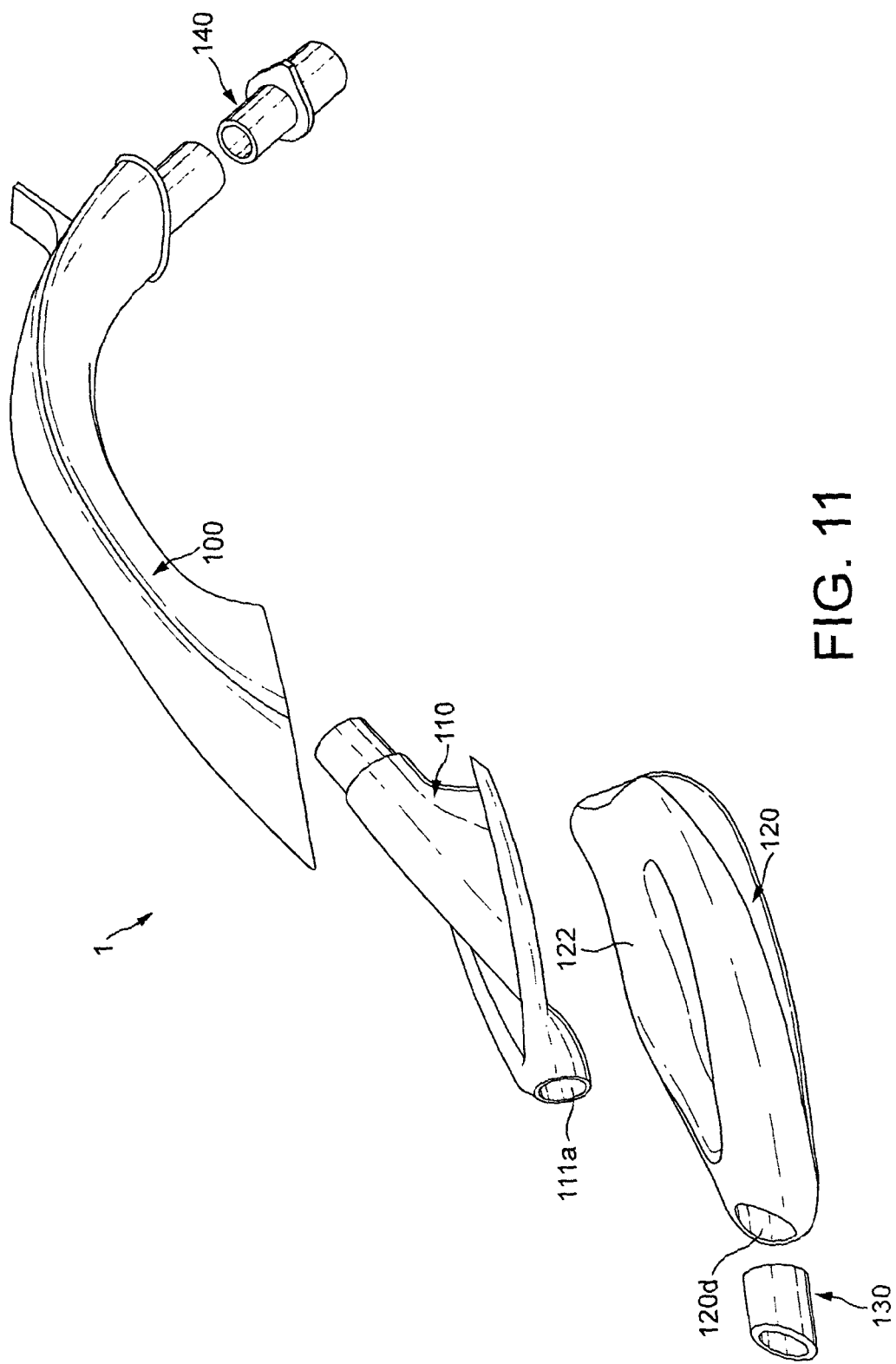

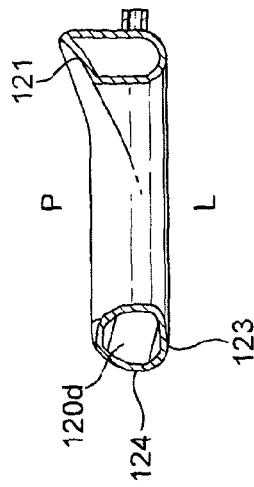
FIG. 14
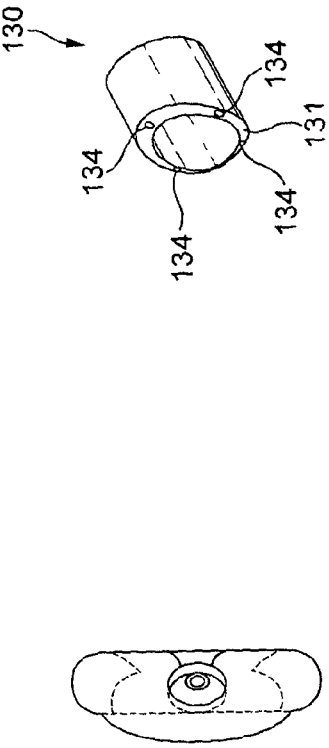
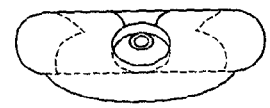
FIG. 17
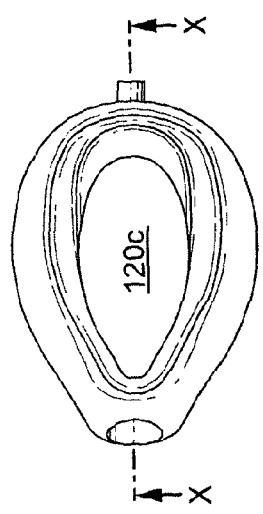
FIG. 13
FIG. 16
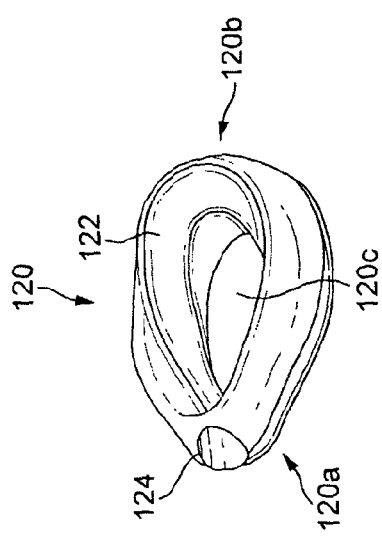
FIG. 12
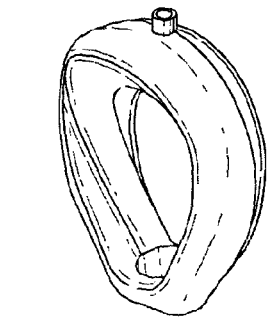
FIG. 15

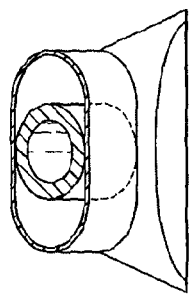
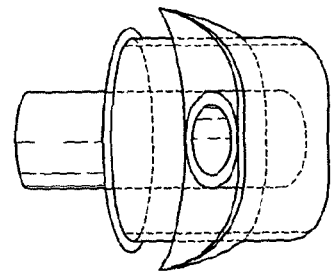
FIG. 28  FIG. 29
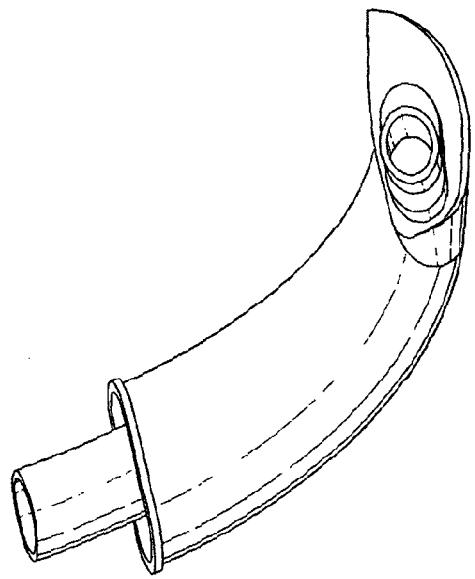
FIG. 30

ARTIFICIAL AIRWAY DEVICE

This application is the U.S. National Phase under 35 U.S.C. §371 of International Application No. PCT/GB2011/001453, filed Oct. 6, 2011, which claims priority to Great Britain Patent Application No. 1017453.0, filed Oct. 15, 2010 and Great Britain Patent Application No. 1115456.4, filed Sep. 7, 2011.

BACKGROUND OF THE INVENTION

The present invention relates to an artificial airway device, and in particular to such a device which seeks to provide protection against gastric reflux.

For at least seventy years, endotracheal tubes comprising a long slender tube with an inflatable balloon disposed near the tube's distal end have been used for establishing airways in unconscious patients. In operation, the endotracheal tube's distal end is inserted through the mouth of the patient, into the patient's trachea. Once positioned, the balloon is inflated so as to form a seal with the interior lining of the trachea. After this seal is established, positive pressure may be applied to the tube's proximal end to ventilate the patient's lungs. Also, the seal between the balloon and the inner lining of the trachea protects the lungs from aspiration (e.g., the seal prevents material regurgitated from the stomach from being aspirated into the patient's lungs).

Although they have been successful, endotracheal tubes suffer from several major disadvantages. The principal disadvantage of the endotracheal tube relates to the difficulty of properly inserting the tube. Inserting an endotracheal tube into a patient is a procedure that requires a high degree of skill. Also, even for skilled practitioners, insertion of an endotracheal tube is sometimes difficult or not possible. In many instances, the difficulty of inserting endotracheal tubes has tragically led to the death of a patient because it was not possible to establish an airway in the patient with sufficient rapidity. Also, inserting an endotracheal tube normally requires manipulation of the patient's head and neck and further requires the patient's jaw to be forcibly opened widely. These necessary manipulations make it difficult, or undesirable, to insert an endotracheal tube into a patient who may be suffering from a neck injury.

The laryngeal mask airway device is a well known device that is useful for establishing airways in unconscious patients, and which seeks to address the above-described drawbacks associated with endotracheal tubes.

In contrast to the endotracheal tube, it is relatively easy to insert a laryngeal mask airway device into a patient and thereby establish an airway. Also, the laryngeal mask airway device is a "forgiving" device in that even if it is inserted improperly, it still tends to establish an airway. Accordingly, the laryngeal mask airway device is often thought of as a "life saving" device. Also, the laryngeal mask airway device may be inserted with only relatively minor manipulation of the patient's head, neck and jaw. Further, the laryngeal mask airway device provides ventilation of the patient's lungs without requiring contact with the sensitive inner lining of the trachea and the internal diameter of the airway tube is typically significantly larger than that of the endotracheal tube. Also, the laryngeal mask airway device does not interfere with coughing to the same extent as endotracheal tubes. Largely due to these advantages, the laryngeal mask airway device has enjoyed increasing popularity in recent years.

U.S. Pat. No. 4,509,514 describes a laryngeal mask airway device which consists of the basic parts which make up most if not all laryngeal mask airway devices, namely an airway tube opening at one end into the interior of a hollow mask portion shaped to fit readily behind the larynx of a patient. The periphery of the mask is formed by a cuff which in use forms a seal around the opening of the larynx. This enables the airway to be established effectively.

Laryngeal mask airway devices with specific provision for gastric-discharge drainage have been developed, as exemplified by U.S. Pat. No. 4,995,388 (FIGS. 7 to 10); U.S. Pat. No. 5,241,956; and U.S. Pat. No. 5,355,879. These devices generally incorporate a small-diameter drainage tube having an end located at the distal end of the mask, so as to lie against the upper end of the upper oesophageal sphincter when the mask is in place, the tube being of sufficient length to extend out of the mouth of the patient to enable active or passive removal of gastric discharge from the upper oesophageal sphincter. According to alternative proposals, the drainage tube may extend beyond the distal end of the mask, into the oesophagus itself (U.S. Pat. No. 4,995,388, FIGS. 7 and 11).

Such devices are generally useful in providing for extraction of regurgitated matter, but are still not always fully effective in preventing aspiration of gastric contents into the patient's lungs. In particular, where the gastric discharge is as a result of the patient vomiting, rather than merely from regurgitation of the gastric matter, the substantial pressure of the vomited matter may in certain cases be enough to dislodge the mask altogether, even where a drainage tube is provided, potentially affecting the integrity of the artificial airway and/or resulting in the vomited matter being aspirated into the lungs of the patient.

As will be appreciated, the potential for the mask to become dislodged under vomiting is also inherent in masks such as that disclosed by U.S. Pat. No. 4,509,514, which do not feature a drainage tube.

Particularly where a mask does not provide for gastric drainage, and even where a gastric drainage tube is provided, there is even a risk of a potentially fatal build up of pressure in the oesophagus if vomited matter cannot be effectively vented from the oesophagus, which might for example occur if the mask becomes jammed in the pharynx.

Previous laryngeal masks designed for example according to U.S. Pat. No. 4,995,388 (FIGS. 7 to 10); U.S. Pat. No. 5,241,956; and U.S. Pat. No. 5,355,879 provided channels to accept regurgitant fluids arising from the oesophagus in which the diameter of the channels is approximately constant and equivalent to the diameter of the constricted area of the anatomy known as the upper oesophageal sphincter. Such devices, once pressed against the sphinctral region provide conditions in which liquids arising from the oesophagus maintain approximately the same velocity as they pass through the tube of the device. Such devices, when correctly positioned, mimic the anatomy of the sphincter, but not that of the oesophagus, in which conditions of lower flow and therefore of higher pressure prevail during reflux of fluids. Such a position of the device may be undesirable however, because the principal object of such devices having a drainage tube communicating with the oesophageal opening is to avoid leakage of any gastric fluids arising from the oesophagus from leaking around the sides of the device, because such leakage risks contamination of the larynx by these fluids with consequent grave risk to the patient.

Furthermore, existing devices provided with gastric drainage tubes do not have tubes with a diameter as great as that of the oesophageal sphincter and therefore can only offer an increase in velocity of fluids entering the drainage tube, which as seen above results in a reduced pressure in the narrower tube, which will tend to cause fluids from the higher pressure region to force the distal end of the device away from the sphincter.

SUMMARY OF THE INVENTION

The present invention seeks to ameliorate problems associated with the prior-art described above.

According to the invention there is provided an artificial airway device to facilitate lung ventilation of a patient, comprising an airway tube, a gastric drain tube and a mask at one end of the at least one airway tube, the mask including a backplate and having a peripheral formation capable of forming a seal around the circumference of the laryngeal inlet, the peripheral formation surrounding a hollow interior space or lumen of the mask and the airway tube opening into the lumen of the mask, wherein the mask includes an atrium for passage to the gastric drain tube of gastric matter leaving the oesophagus. As will be appreciated, the atrium provides an enlarged space or conduit that potentially substantially reduces the risk of the mask becoming dislodged on the occurrence of regurgitation or vomiting of matter, allowing the integrity of the airway to be maintained, and thereby potentially greatly minimises the risk of gastric insuflation.

It is preferred that the atrium is defined by a part of the backplate, and in particular that the defining part is a wall of the backplate. This provides a compact construction that utilises existing mask structures to provide the gastric conduit. The wall may comprise an outer skin and an inner skin, the atrium being formed between the skins and the skins may be formed from a resiliently deformable material that is softer in durometer than the material of the airway tube to aid in insertion.

In a particularly preferred embodiment the outer skin comprises a part of the gastric drain tube and the inner skin comprises a part of the airway tube, which again utilises existing structures. The said part of the gastric drain tube may be an integrally formed part thereof, to assist in manufacture and the said part of the airway tube may include a bore in fluid communication with the lumen of the mask.

Conventionally in laryngeal mask construction the gastric drain is provided as a tube within the airway tube, chiefly because it has been felt to be most important to retain as large a bore as possible for passage of gasses whilst also providing a compact structure to fit within the anatomy. In the present instance it has been found unexpectedly that the airway tube can be disposed within the gastric drain tube without loss of performance as an airway, and with the added benefit that a larger gastric drain conduit, and even more than one gastric drain conduit can be provided. In one embodiment of the invention the airway tube may be disposed to establish a separation of the space within the gastric drain tube into two gastric conduits.

According to a second aspect of the invention there is provided an artificial airway device to facilitate lung ventilation of a patient, comprising an airway tube, a gastric drain tube and a mask at one end of the at least one airway tube, the mask including a backplate and having a peripheral formation capable of forming a seal around the circumference of the laryngeal inlet, the peripheral formation surrounding a hollow interior space or lumen of the mask and the airway tube opening into the lumen of the mask, the device being adapted to allow for a visual inspection of its contents when the device is removed form the patient. This may be achieved by the provision of a transparent or even translucent backplate outer wall skin. This enables a user to easily discover the cause of a blockage.

According to a third aspect of the invention there is provided an artificial airway device to facilitate lung ventilation of a patient, comprising an airway tube, a gastric drain tube and a mask at one end of the airway tube, the mask including a backplate, gastric drainage conduit and having a peripheral formation capable of forming a seal around the circumference of the laryngeal inlet, the peripheral formation surrounding a hollow interior space or lumen of the mask and the airway tube opening into the lumen of the mask, the gastric drainage conduit including an inlet, the mouth of the inlet being formed such that it is disposed substantially normal to the axis of the oesophageal sphincter of the patient when the device is in situ. This helps achieve a more effective seal with the oesophageal sphincter.

Thus the advantages of the above described arrangements include, for example, less complicated manufacturing than in prior structures that include tubes or tubular formations in the backplate. Furthermore, the stiffness of the backplate is reduced when compared to previous structures involving backplate tubes, thus aiding ease of insertion. Having the conduit provided by the backplate in this manner also provides a conduit of large and expandable volume such that displacement of the device under vomiting is less likely to occur, particularly where the outer skin, or both skins of the conduit are formed from a softly pliant resiliently deformable material.

The device may include a plurality of gastric drain tubes, each said tube being in fluid communication with the atrium. This allows for application of suction to one of the tubes, in use. It is particularly preferred that the device includes two drain tubes. Where only a single gastric drain tube has been used in prior devices it has been found that damage to delicate structures of the anatomy such as the oesophageal sphincter can occur when suction is applied. In the present design, the presence of a plurality of gastric drain tubes ensures that when suction is applied to one tube to remove gastric material in the atrium, the other gastric tube allows air to be drawn into the atrium rather than the patient's anatomy.

Where the device includes two gastric drain tubes it is preferred that the tubes are disposed in side by side relation with the airway tube therebetween, the drain tubes and airway tube together defining a pocket disposed to accommodate a patient's tongue when the device is in use. This makes the device more comfortable for the patient. Where the airway tube comprises (as is desirable) a more rigid material than the drain tubes, the airway tube thus provides support to the drain tubes that may remove the need for a biteblock, thus again simplifying manufacturing and saving cost.

In an alternative embodiment, the device may comprise a single gastric drain tube in fluid communication with the atrium. It is preferred that the drain tube comprises a softly pliant collapsible material. The drain tube may be disposed on a surface of the airway tube, or around the airway tube, for support.

It is preferred that the peripheral formation comprises an inflatable cuff, or a non-inflatable cuff. It is further preferred that where the peripheral formation comprises an inflatable cuff, the backplate overlies the cuff and is bonded to it, such that on deflation the cuff may be collapsed upon it, thereby encouraging the cuff to pack flat.

BRIEF DESCRIPTION OF THE DRAWINGS

The invention will now further be described by way of example, with reference to the accompanying drawings, in which:

FIG. 8 is a dorsal three quarter perspective view of a further alternative embodiment of device according to the invention;

FIG. 9 is a longitudinal sectional view of the device of FIG. 8;

FIG. 10 is a longitudinal sectional view of the device of FIG. 8;

FIGS. 10a to 10f are transverse sectional views taken along lines 1 to 6 in FIG. 10;

FIG. 11 is an exploded view of the device of FIG. 8;

FIG. 12 is a front three quarter perspective view of a part of the device of FIG. 8;

FIG. 13 is a plan view of the part of FIG. 12;

FIG. 14 is a transverse sectional view along line X-X in FIG. 13;

FIG. 15 is a rear three quarter perspective view of the part of FIG. 12;

FIG. 16 is a rear end view of the part of FIG. 12;

FIG. 17 is a front perspective view of a part of the device of FIG. 8;

FIG. 28 is a transverse sectional view along line B-B in FIG. 26;

FIG. 29 is a front view of the part of FIG. 26;

FIG. 30 is a front perspective view of the part of FIG. 26;

DETAILED DESCRIPTION OF THE PREFERRED EMBODIMENT

Figure 1:
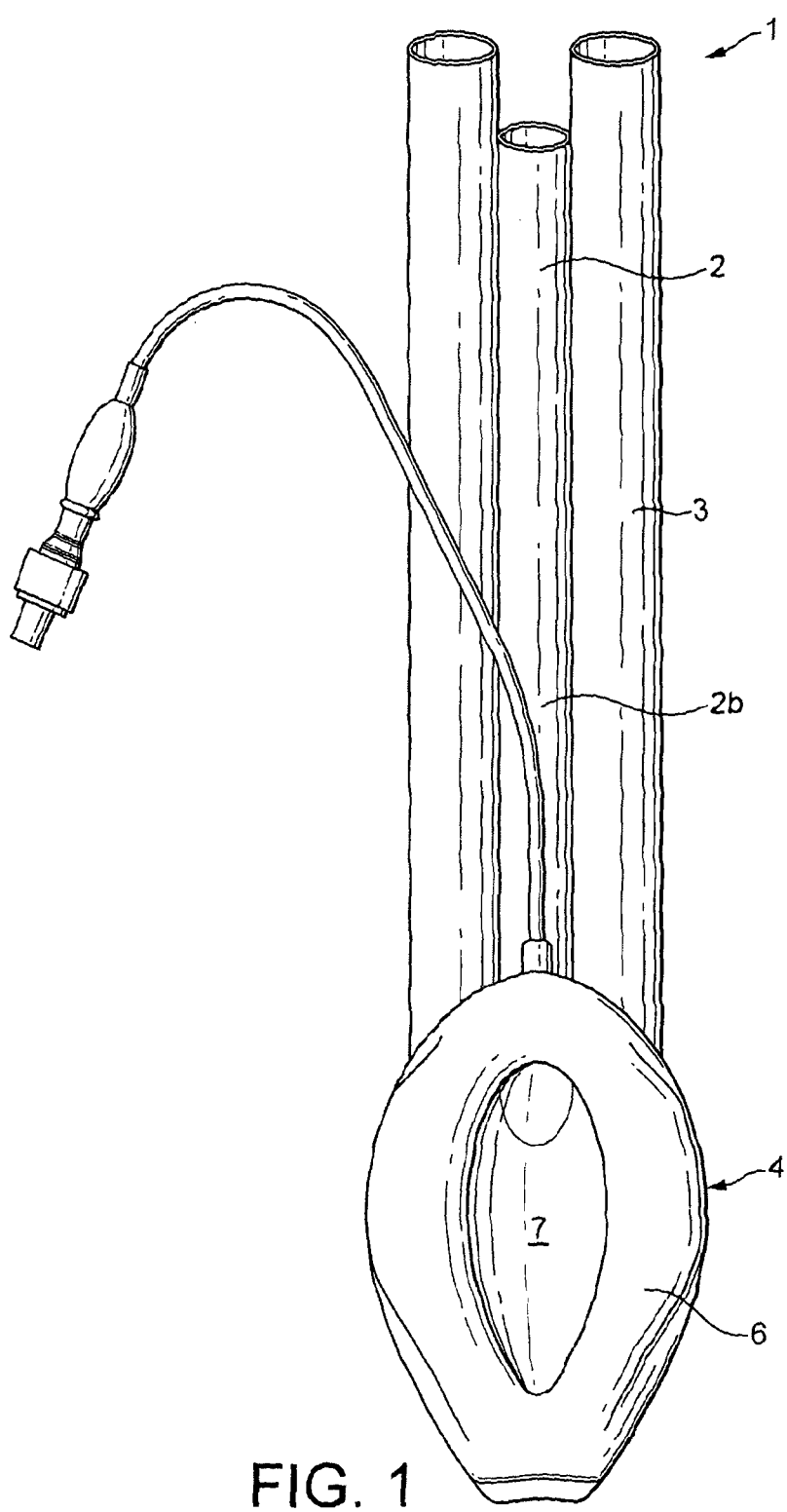
FIG. 1 is a ventral view of a device according to the invention.

In the discussion of the following exemplary embodiments, like parts will generally be given the same reference numerals throughout the description.

Referring to the drawings, there is illustrated an artificial airway device 1 to facilitate lung ventilation of a patient, comprising an airway tube 2, a gastric drain tube 3 and a mask 4 at one end of the airway tube 2, the mask 4 including a backplate 5 and having a peripheral formation 6 capable of forming a seal around the circumference of the laryngeal inlet, the peripheral formation 6 surrounding a hollow interior space 7 or lumen of the mask 4 and the at least one airway tube 2 opening into the lumen of the mask, wherein the mask includes an atrium 8 for passage to the gastric drain tube 3 of gastric matter leaving the oesophagus.

Figure 2:
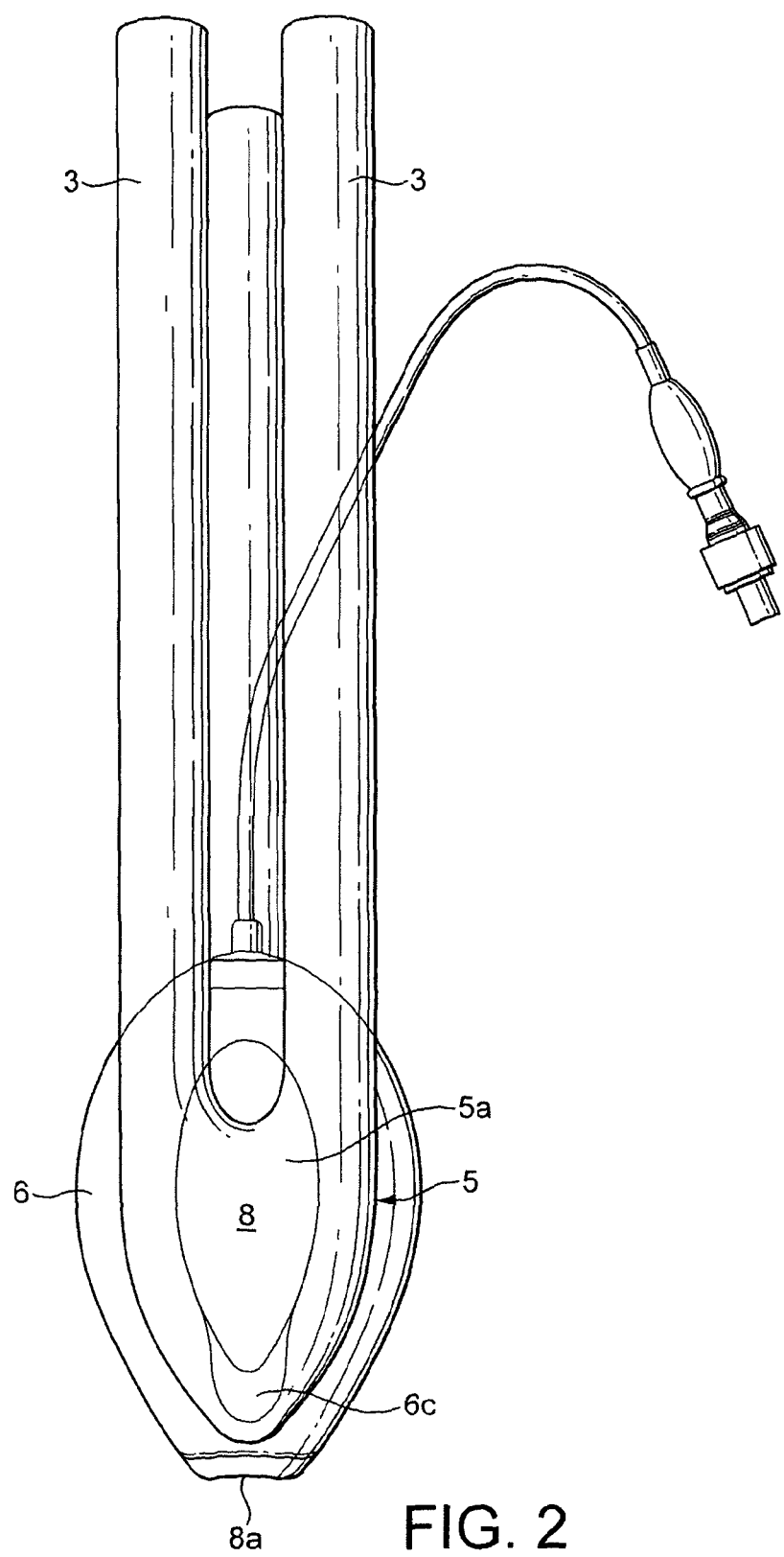
FIG. 2 is a dorsal view of the device of FIG. 1.

For convenience, the surface of the device illustrated in FIG. 1 is herein referred to as the dorsal surface and the surface of the device illustrated in FIG. 2, which is the opposite surface to that shown in FIG. 1, is referred to as the ventral surface. In accordance with standard practice, the part of the device 1 that in use will extend from the patient is referred to herein as the proximal end (in the sense that it is nearest the user) with the other end being referred to herein as the distal end.

Figure 3:
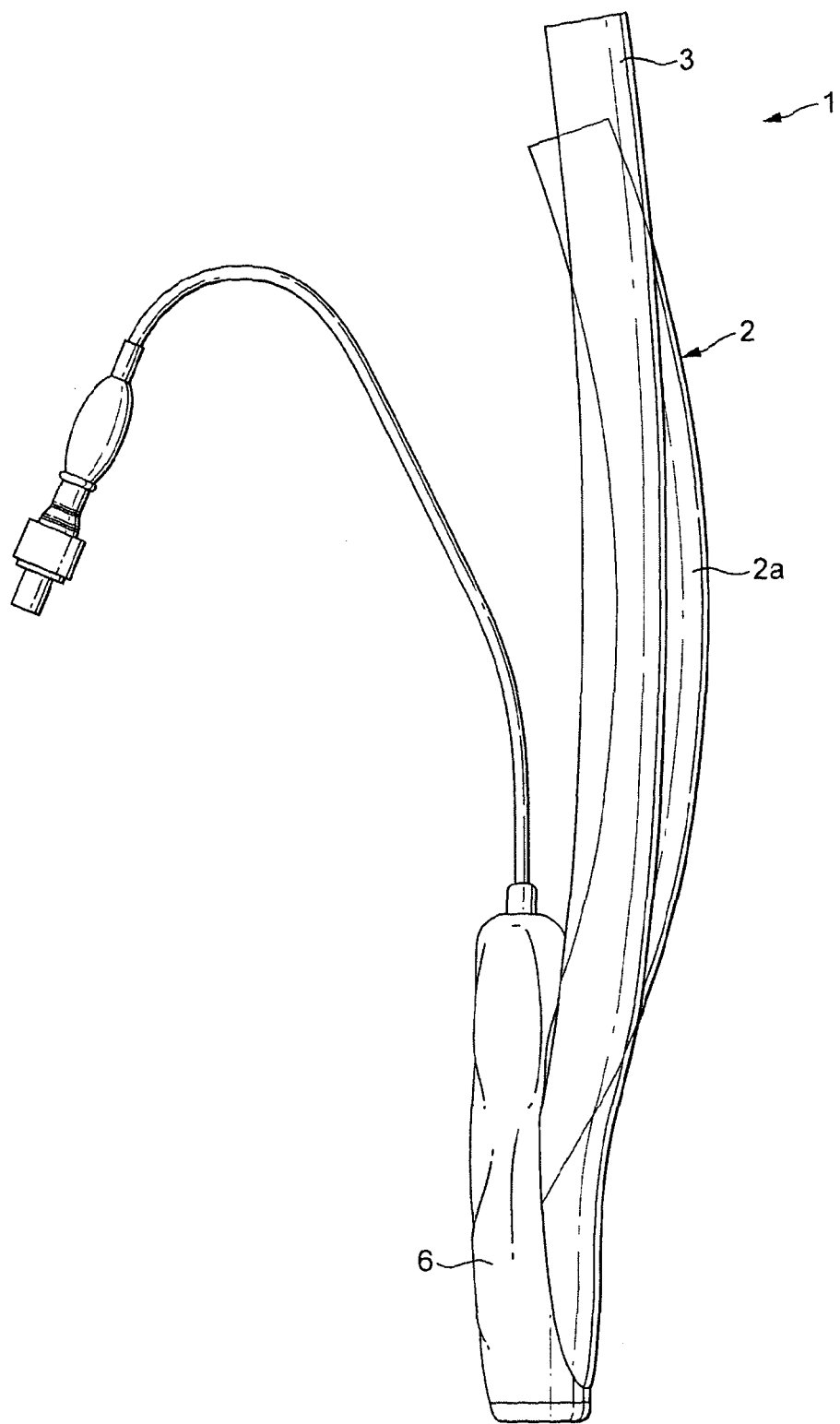
FIG. 3 is a side view of the device of FIG. 1.

Referring in particular to FIGS. 1 to 6, the device 1 as illustrated includes two gastric drain tubes 3 disposed on either side of airway tube 2 and bonded thereto. It is preferable that the drain tubes 3 are formed from a sufficiently soft resiliently deformable material to be collapsible so that insertion of the device is made easier and also that the space within the anatomy required to accommodate the device in situ is minimised. As an example, the material of the gastric drain tubes 3 is preferably of 20 to 30 Shore durometer. Airway tube 2 is formed from a more rigid material than the drain tubes 3 such that it is not collapsible and has a preformed fixed curve as illustrated in FIG. 3. As an example, the airway tube 2 may be of 80 Shore durometer. It is bonded to the drain tubes such that a portion 2a of its length protrudes dorsally thereabove. As will be appreciated, this forms a hollow or pocket 2b on the ventral side. The drain tubes and airway tube may be formed from any known suitable material.

At its distal end, airway tube 2 is attached to mask 4. Airway tube 2 and mask 4 may be formed integrally or separately. It will be noted, particularly from FIGS. 5 and 6, that airway tube 2 terminates towards the proximal end of mask 4 at 2c. Thus mask 4 does not suffer in terms of being made too rigid by the material of the airway tube. Mask 4 includes a backplate 5 that is formed integrally with drain tubes 3. One notable feature of the present invention is the construction of the backplate. As the skilled worker will appreciate, the term "backplate", when used in the present technical field has come to denote that part of the mask that is surrounded by the cuff in the assembled device and which provides separation between the laryngeal and pharyngeal regions when the device is in situ in the patient. Supply of gas takes place through an aperture in the backplate via a fluid tight connection between the part of the backplate defining the aperture and the airway tube. In one known arrangement the backplate and airway tube are formed integrally which is a particularly convenient arrangement. In the prior art, backplates are generally bowl or dome shaped structures rather than flat structures and the term is therefore not entirely descriptive of the shape.

Figure 4:
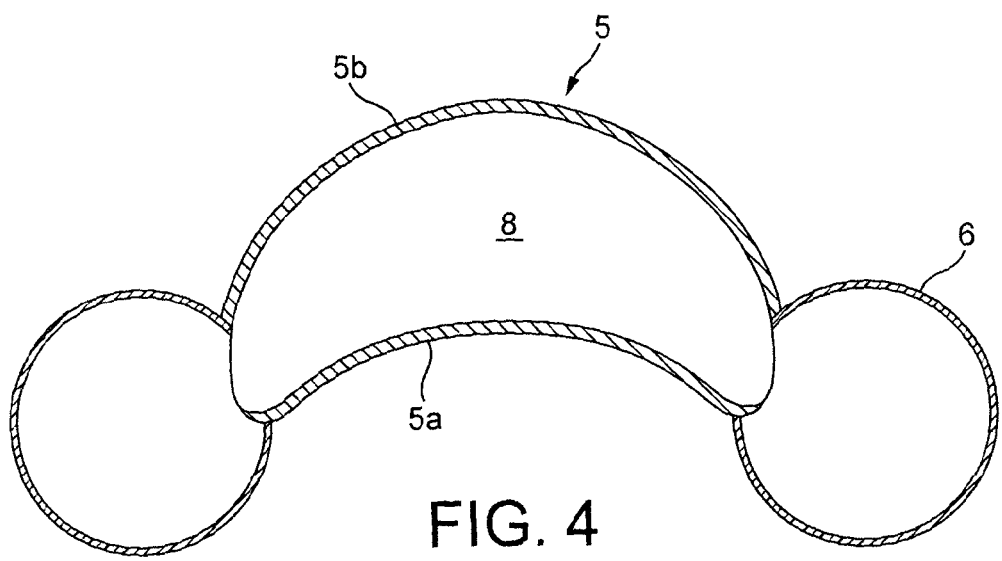
FIG. 4 is schematic transverse sectional view of a part of a device according to the invention.
Figure 5:
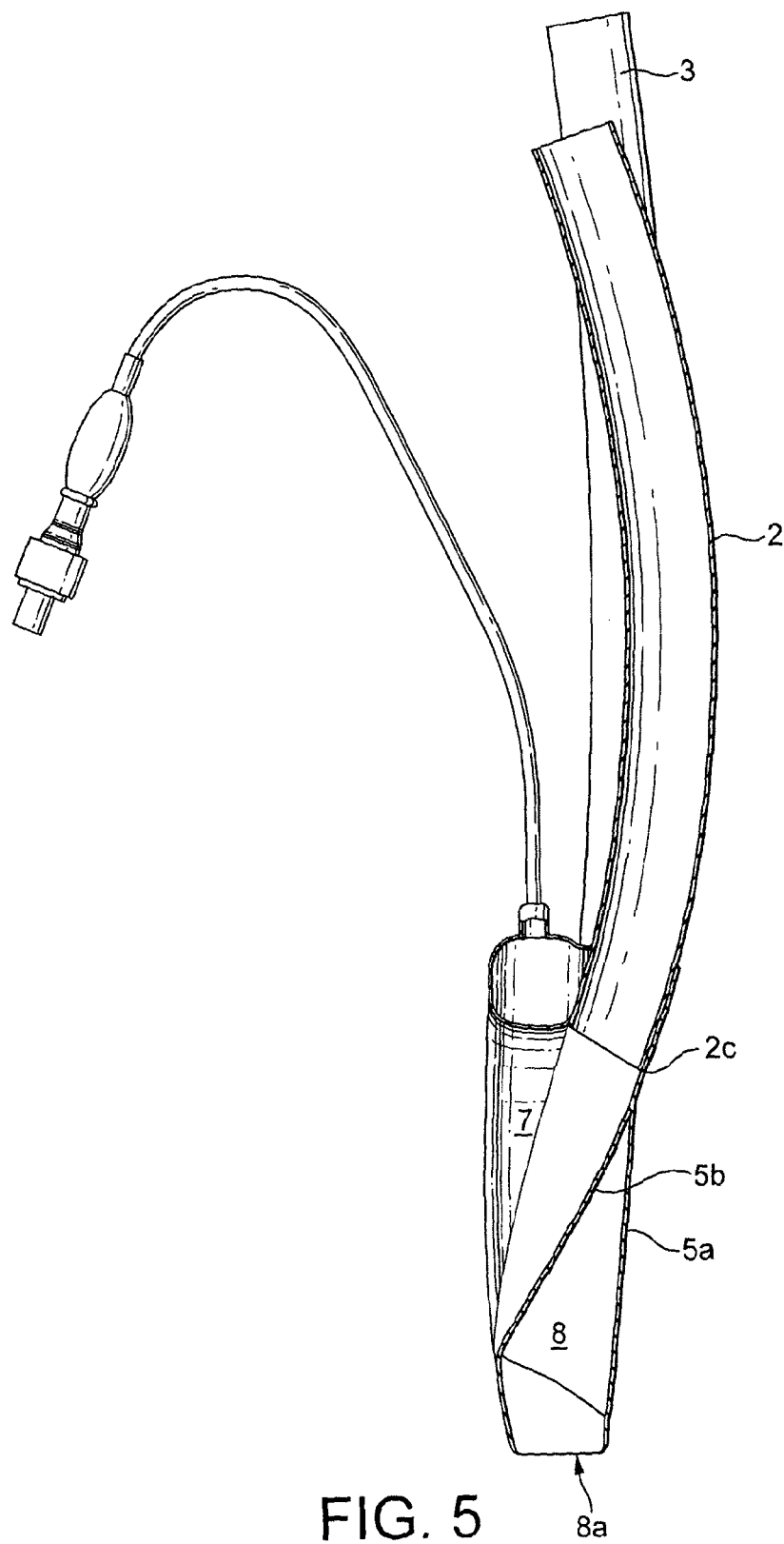
FIG. 5 is a longitudinal sectional view of the device of FIG. 1.
Figure 6:
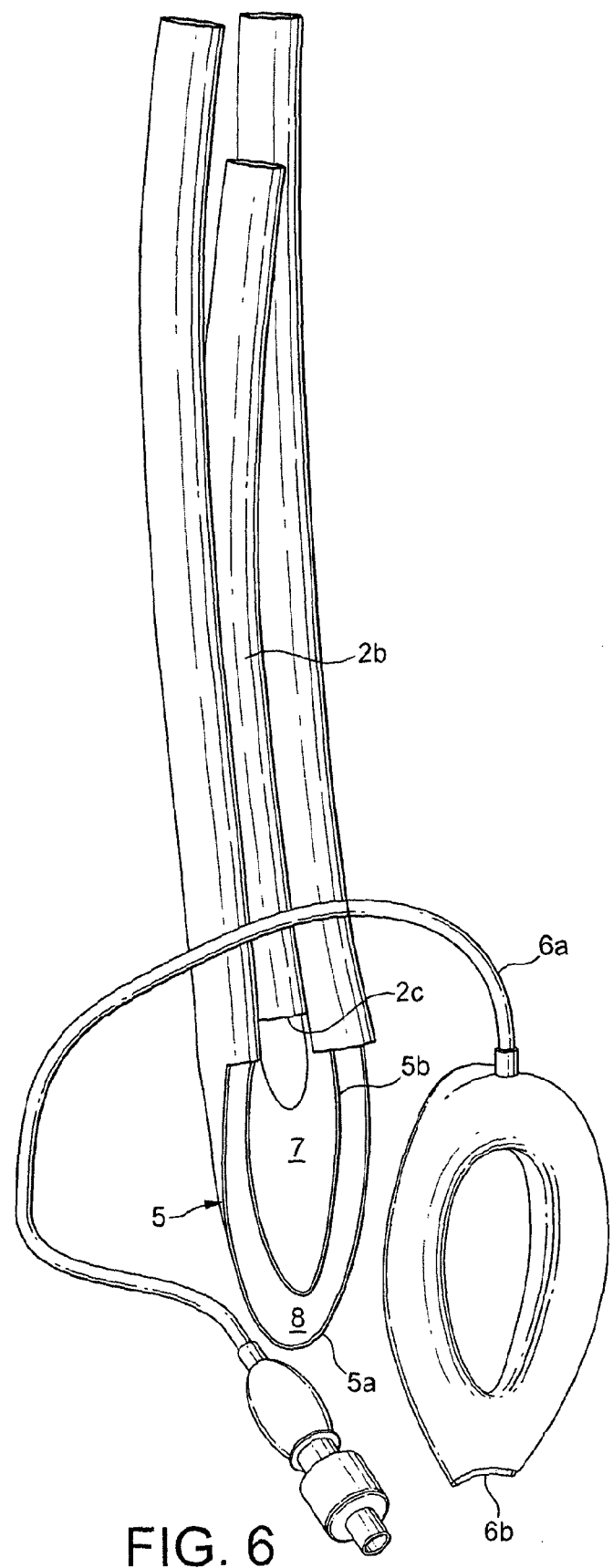
FIG. 6 is an exploded view of the device of FIG. 1.

In the presently described embodiment backplate 5 comprises inner and outer skins 5a, 5b that together define a space therebetween, as shown schematically in FIG. 4. The space so defined is atrium 8 from which proximally, drain tubes 3 lead off and distally, inlet 8a enters (as shown in FIG. 2). Thus atrium 8 can be regarded as a manifold that connects the single gastric inlet 8a with the two gastric drain tubes 3. One method of constructing the mask 4 is illustrated in FIG. 6, from which it can be seen that the gastric drain tubes 3 and backplate 5 are integrally formed. It will be appreciated that in the illustrations the material from which the backplate 5 and drain tubes 3 are formed is transparent to aid in understanding of the construction of the device 1.

As mentioned above, mask 4 includes peripheral formation 6 which in this embodiment takes the form of an inflatable cuff of generally known form. Cuff 6 includes an inflation line 6a at its proximal end and has a gastric inlet aperture 6b at its distal end that communicates via a bore with an inner aperture 6c (FIG. 2). The bore is defined by a collapsible tube. Means may be provided to keep the tube collapsed until the cuff is inflated, such as a press-stud or "ziplock" arrangement. Referring to the exploded view in FIG. 6, it can be seen that the dorsal surface of Cuff 6 is bonded to backplate 5 so that the material of the dorsal surface of the cuff 6 forms a bridge between the inner and outer skins 5a, 5b thus closing off the ventral side of atrium 8 except where gastric inlet aperture 6b enters the cuff. Thus it can be seen that gastric inlet 6b is in fluid communication with atrium 8 via aperture 6c. In an alternative method of construction the cuff 6 may be formed with a web across its aperture that itself forms the ventral surface of atrium 8.

Figure 7:
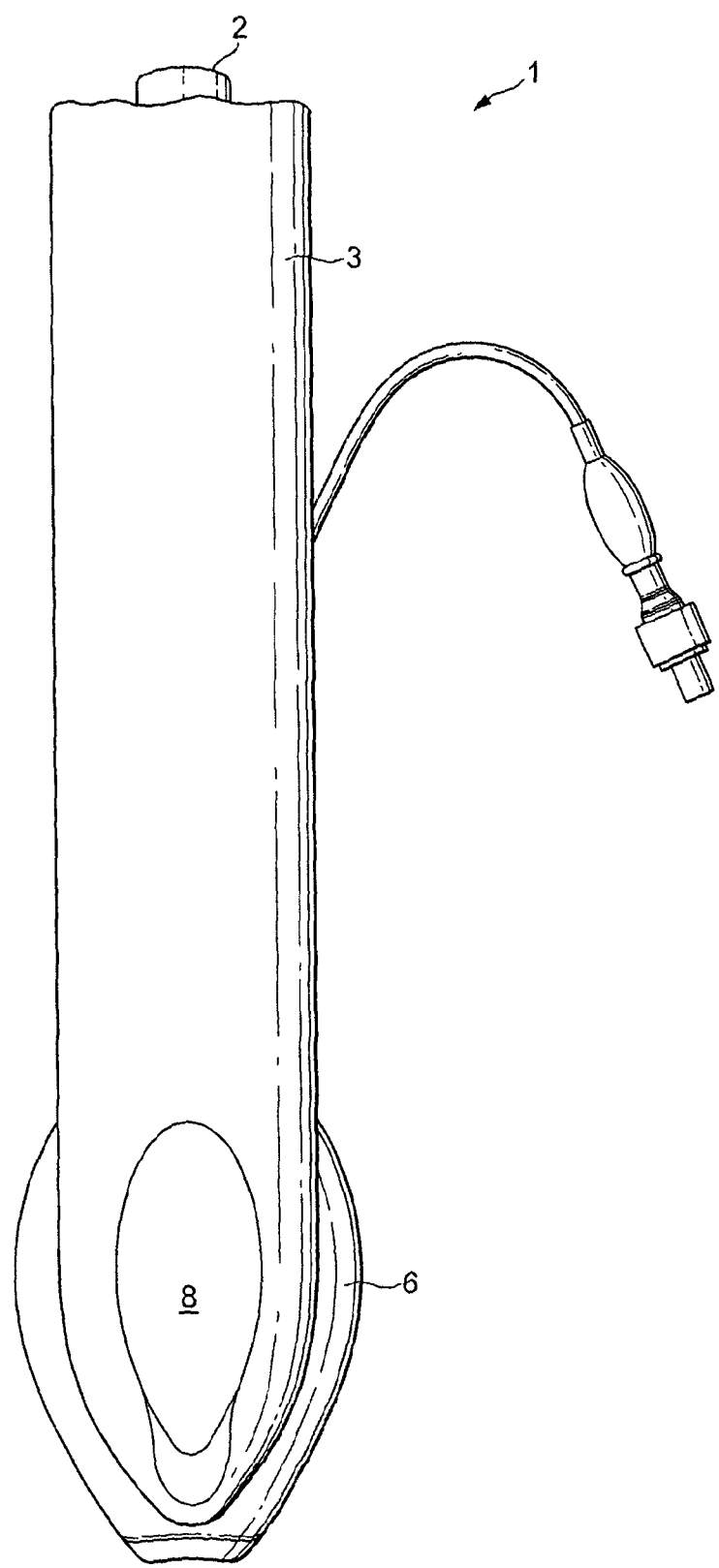
FIG. 7 is a dorsal view of an alternative embodiment of device according to the invention.

Referring now to FIG. 7, there is illustrated an alternative embodiment of device 1. In this embodiment the device includes a single gastric drain 3 in the form of a softly pliant sleeve that terminates at its distal end in atrium 8, all other features of construction being the same as in the first described embodiment hereinabove.

In use, the device 1 is inserted into a patient to establish an airway as with prior art devices. Insertion is effected to the point where gastric inlet aperture 6b meets the patient's oesophageal sphincter, thus establishing fluid communication therebetween. If vomiting or regurgitation occurs, as with previous gastric access laryngeal masks, the material from the oesophagus passes into gastric inlet aperture 6b. However, unlike with previous devices the material passes into the atrium 8 formed between the dual backplate skins 5a 5b, the volume of which is larger than the volume of the inlet aperture 6b. It will be appreciated that constructing a laryngeal mask with a backplate 5 in which is formed an atrium or conduit 8 for gastric material is a highly efficient and economical way to use existing mask structures. Forming gastric drain tubes from an expandable material so that the space they occupy in the anatomy is minimised until they are called upon to perform their function is advantageous because it makes insertion of the device easier and causes less trauma to the delicate structures of the anatomy when the device is in place, particularly if the device is left in place for an extended period. And still further advantages are obtained if these features are combined such that the atrium 8 is formed from the soft material of the gastric drain tubes makes because the mask, whilst being sufficiently soft to avoid trauma on insertion can yet provide a large volume atrium 8 that can expand under pressure of vomiting. Such expansion results in a dorsal deformation of the outer skin 5b resembling a dome (FIG. 4) that acts like a spring against the back wall of the throat when the mask is in situ, forcing the cuff 6 against the larynx and thereby helping to maintain the device in its sealed state.

Referring now to FIGS. 8 to 33, there is illustrated a further alternative embodiment of device 1 according to the invention. This embodiment differs from the previously described embodiment in a number of important respects as will be described. However it will be appreciated that the concepts which it embodies may be applied to the previously described embodiments and vice versa.

Referring in particular to FIGS. 8 and 9, there is illustrated an artificial airway device 1 to facilitate lung ventilation of a patient, comprising an airway tube 2, a gastric drain tube 3 and a mask 4 at one end of the airway tube 2, the mask 4 including a backplate 5 and having a peripheral formation 6 capable of forming a seal around the circumference of the laryngeal inlet, the peripheral formation 6 surrounding a hollow interior space 7 or lumen of the mask 4 and the at least one airway tube 2 opening into the lumen of the mask, wherein the mask includes an atrium 8 for passage to the gastric drain tube 3 of gastric matter leaving the oesophagus.

It can be seen that the device 1 resembles other laryngeal mask airway devices. However, from the exploded view of FIG. 11 it can be seen that the device 1 comprises three main parts, a gastric drain and airway tube and backplate combination part 100, an inner backplate wall 110, a peripheral formation 120, and two minor parts, an inlet ring 130 and a connector 140.

Figure 24:
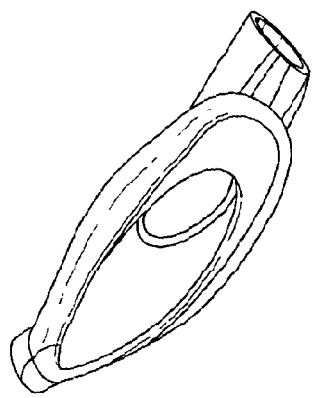
FIG. 24 is an underplan perspective view of the part of FIG. 20.
Figure 25:
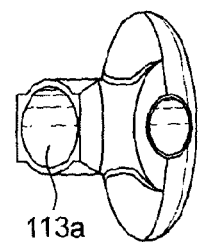
FIG. 25 is a front end view of the part of FIG. 20.
Figure 26:
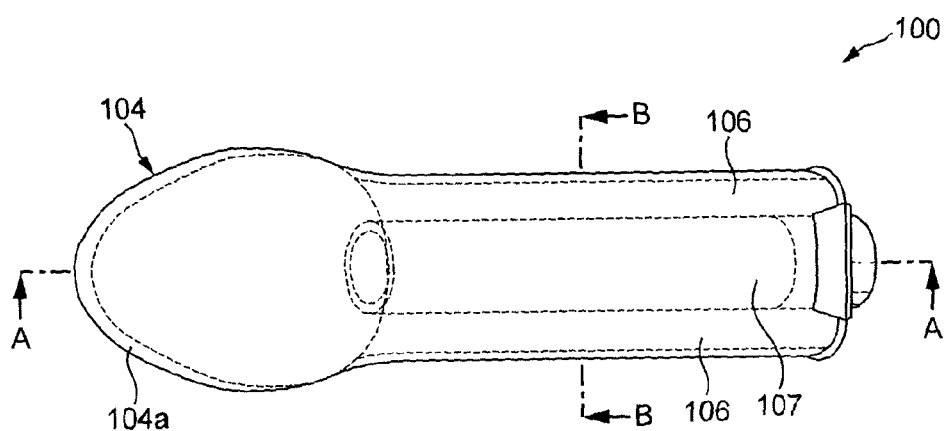
FIG. 26 is an underplan view of a part of the device of FIG. 8.
Figure 27:
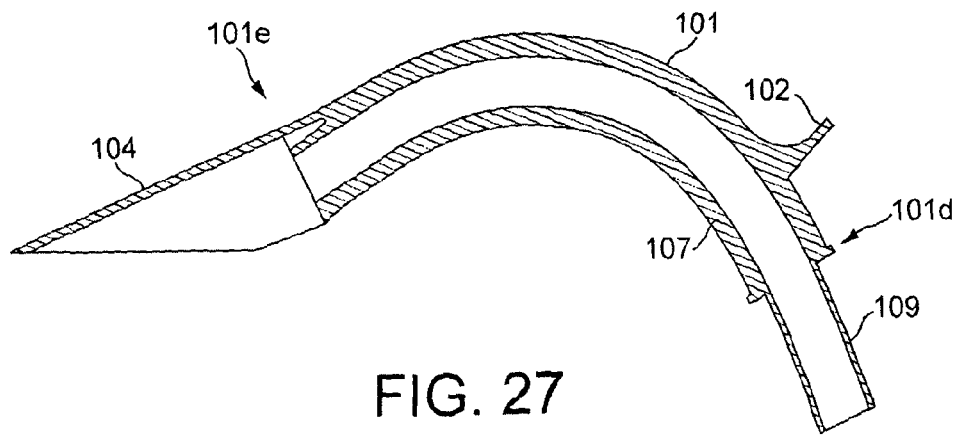
FIG. 27 is a longitudinal sectional view along line A-A in FIG. 26.
Figure 31:
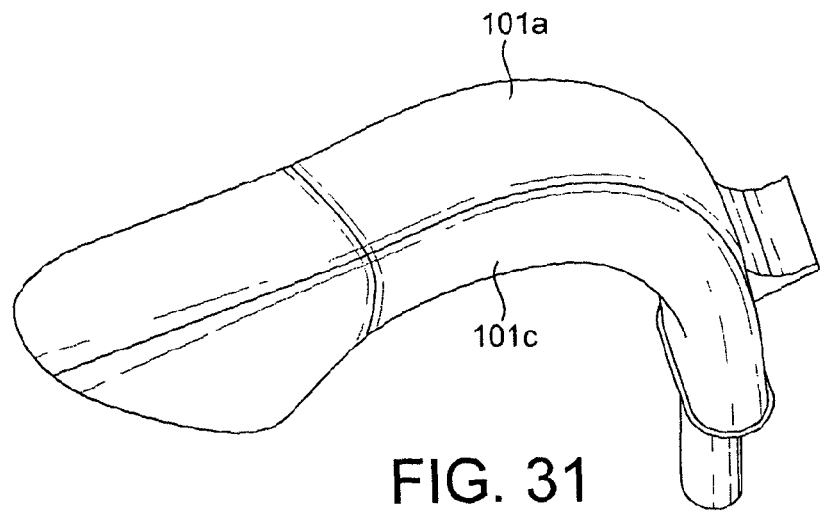
FIG. 31 is a plan perspective view of the part of FIG. 26.
Figure 32:
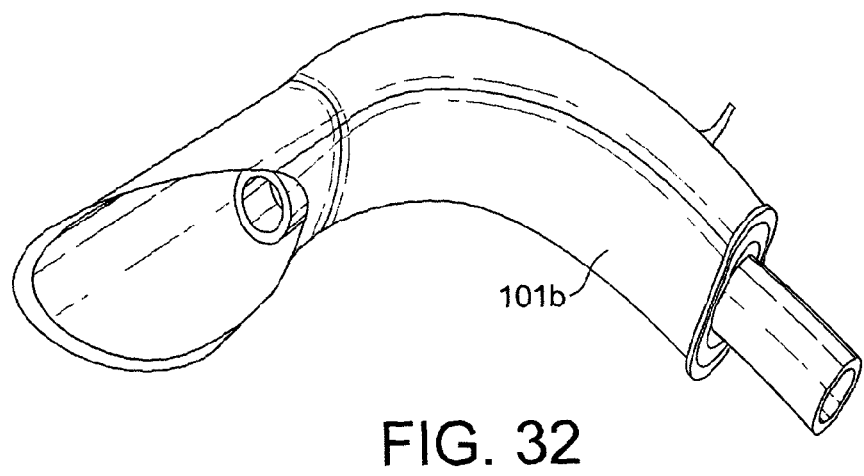
FIG. 32 is an underplan perspective view of the part of FIG. 26.
Figure 33:
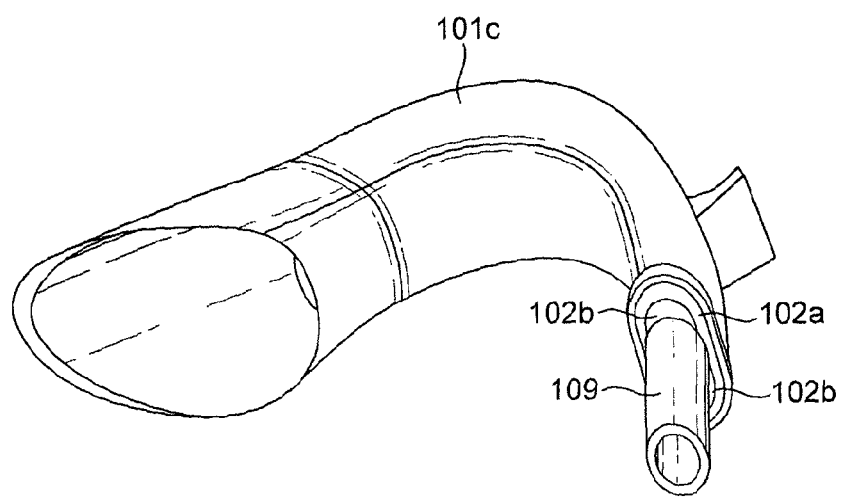
FIG. 33 is a rear perspective view of the part of FIG. 26.

Referring now to FIGS. 26 to 33, the gastric drain and airway tube and backplate combination part 100 will be described. This combination part 100 consists of a precurved tube 101. The tube 101 is not circular in cross-section but has a flattened section, as taught in previous patents, for ease of insertion and fit through the interdental gap. The tube 101 has flattened dorsal and ventral surfaces 101a, 101b and curved side walls 101c extending from a proximal end 101d to a distal end 101e. Towards the proximal end 101d on the dorsal surface there is disposed a fixation tab 102 and at the end is attached a plate 102a (FIG. 33). Plate 102a includes three apertures, two gastric apertures 102b either side of an airway aperture through which an airway conduit 107 extends. At its distal end the combination part 100 is cut at an angle relative to its longitudinal axis to provide a flared outer backplate part 104 integrally formed therewith, for example by molding. As an alternative the flared backplate part 104 can be separately formed, in particular from a transparent or translucent material. The backplate part 104 includes a circumferential lip 104a. Finally, it will be noted that combination part 100 includes a substantially coaxially disposed inner tube extending from the distal end to the proximal end, the inner tube effectively establishing a separation of the inner space into two gastric conduits 106 and an airway conduit 107. It will be noted that unlike in prior art constructions, this results in an airway conduit 107 contained within a gastric drain conduit. In the longitudinal sectional view shown in FIG. 27 it can be seen that the airway conduit 107 terminates in a cylindrical connector extension 109 at its distal end. Referring now to FIGS. 20 to 25, there is illustrated inner backplate wall 110. Inner backplate wall 110 comprises a generally elliptical body in the form of a shallow dish including side wall 111 and floor 112. At the distal, or narrower end of the elliptical dish, side wall 111 has a cylindrical aperture 111a formed therein that extends distally generally in line with the midline of the floor 112. It will be noted that cylindrical aperture 111a is angled upwardly, relative to the plane of the floor 112 such that the angle of the axis of the bore of the cylindrical aperture is about 20 degrees relative thereto. Along its midline the floor 112 of the dish is raised to form a convex surface that extends longitudinally towards the wider, proximal end where it terminates in a cylindrical formation that may be referred to as a tube joint 113. Tube joint 113 includes bore 113a that provides a connecting passage between the upper and lower surfaces (as viewed) of floor 112. Tube joint 113 merges with and bisects side wall 111 and is angled upwardly at about 45 degrees relative to floor 112, terminating proximally some distance beyond the side wall 111 as shown in FIG. 24.

Referring now to FIGS. 12 to 16, there is illustrated peripheral formation 120 which in this embodiment takes the form of an inflatable cuff. It will be noted that unlike many other laryngeal mask airway devices the cuff 120 is formed integrally as a separate part from the rest of the device, making it easier both to manufacture and attach to the device 1. The cuff 120 comprises a generally elliptical body with a narrower distal end 120a, a wider proximal end 120b and a central elliptical through-aperture 120c. As such it will be appreciated that the cuff resembles a ring. As can be seen from the sectional view in FIG. 14, the elliptical body comprises a wall 123 that is generally circular in section at the distal end but deeper and irregularly shaped at the proximal end by virtue of an integrally formed extension 121 formed on the dorsal surface at the proximal end 120b. This dorsal surface extension 121 defines the proximal portion of an attachment surface 122 (FIGS. 11 and 12). The attachment surface 122 extends from the proximal end to the distal end around the entire dorsal inner circumference of the ring. At its distal end 120a the cuff has a cylindrical through bore 121 the axis of which extends in line with the midline of the ellipse and is angled upwardly as viewed in FIG. 14 relative to the plane of the body, in other words from the ventral towards the dorsal side or when the device 1 is in use from the laryngeal to the pharyngeal side of the anatomy (L and P in FIG. 14). The result is a circular section aperture through the cuff wall 123. The proximal end 120b of the cuff includes a port 124 that lets into the interior of the bore and the cuff.

Figure 18:
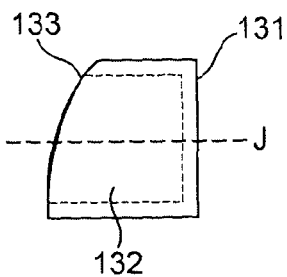
FIG. 18 is a side view of the part of FIG. 17.
Figure 19:
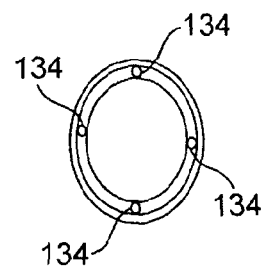
FIG. 19 is an end view of the part of FIG. 17.
Figure 20:
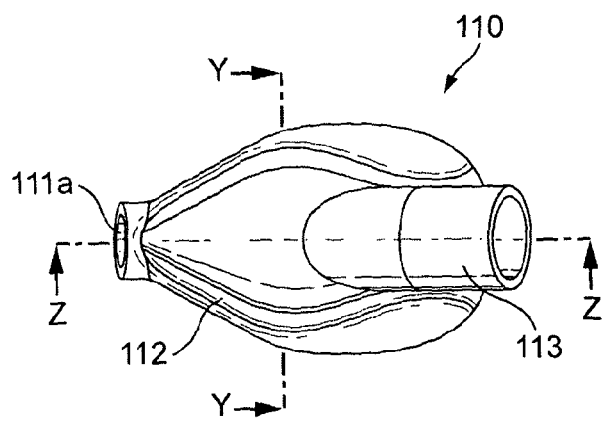
FIG. 20 is a plan view of a part of the device of FIG. 8.
Figure 21:
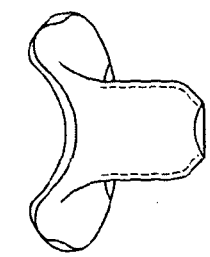
FIG. 21 is a transverse sectional view along line Y-Y of FIG. 20.
Figure 22:
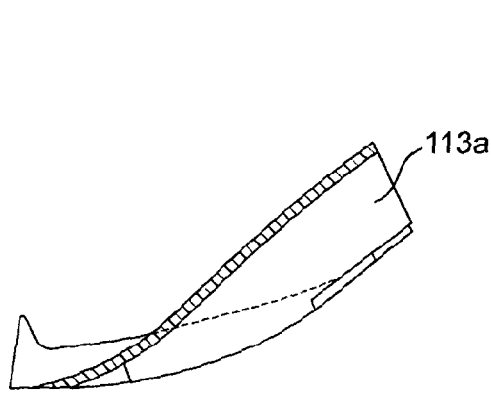
FIG. 22 is a longitudinal view along line Z-Z of FIG. 20.
Figure 23:
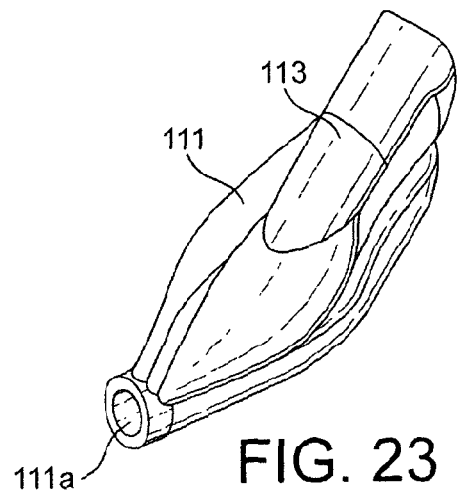
FIG. 23 is plan perspective view of the part of FIG. 20.

Referring now to FIGS. 17 to 19 there is illustrated inlet ring 130. Inlet ring 130 is a cylindrical section tube having a proximal end 131 cut normal relative to the axis "J" of bore 132 of the tube. The distal end 133 is cut obliquely, relative to the axis "J" of the bore 132, the cut extending back from the ventral to the dorsal side as viewed. It will be seen that the obliquely cut distal end 132 has a shallow curve, rather than being a straight cut. The wall of the cylinder includes minor open through bores 134 that extend the length of the cylinder and are open at each end.

FIG. 11 illustrates how the parts of device 1 fit together and is most usefully viewed in combination with FIGS. 8 and 9. From these it can be seen that the combination part 100, and inner backplate wall 110 are combined to form the backplate 5, thus defining a conduit in the form of chamber or atrium 8 within the backplate 5. The peripheral part 120, in this embodiment an inflatable cuff, is attached to the backplate 5 by bonding to the attachment surface 122 such that the backplate 5 seats within it. The connector 130 is passed through the cylindrical bore 121 in the cuff wall and affixed therein in connection with the cylindrical aperture 111a.

As mentioned, the embodiment of FIGS. 8 to 33 differs from prior art devices in a number of important respects. For example, in this device the airway tube 107 is contained within the gastric drain tube whereas in prior art devices the opposite is the case. It has been found that contrary to expectation it is most important in a device having a gastric tube that flow of gastric material should not be impeded, so that the seal formed around the upper oesophageal sphincter is not broken. This arrangement best utilises the available space within the anatomy to achieve this end. Similarly, the provision of an atrium 8 to receive gastric flow as opposed to the simple uniform section conduits of prior devices provides a mask that is in effect a hollow leak-free plug against the upper oesophageal sphincter, with a low-flow high-volume escape route above it. The device 1 of this embodiment of the invention enables a user to get such a plug into place and hold it there whilst providing a sufficiently generous escape path for emerging fluids. Further still, it has been found that the provision of a gastric inlet port that is angled dorsally as described further aids in ensuring that the seal around the upper oesophageal sphincter remains intact even under heavy load, particularly when an atrium is provided directly upstream therefrom.

Thus, it can be seen that the above described embodiments address the problems of prior art devices in novel and inventive ways.

Features of the above-described embodiments may be re-combined into further embodiments falling within the scope of the present invention. Further, the present invention is not limited to the exemplary materials and methods of construction outlined above in connection with the exemplary embodiments, and any suitable materials or methods of construction may be employed. For example, although the cuff may be formed using a sheet of soft flexible silicone rubber, other materials such as latex or PVC may be used. PVC as a material is particularly suited to embodiments intended for single use, whereas the use of silicone rubber is preferred although not essential for embodiments intended to be re-used in a number of medical procedures.

Further, and as would be appreciated by the skilled person, various features of the present invention are applicable to a wide range of different laryngeal mask airway devices, and the invention is not limited to the exemplary embodiments of types of mask described above. For example, aspects of the invention may be applied to laryngeal mask airway devices featuring epiglotic elevator bars over the mask aperture, which bars are operable to lift the epiglottis of a patient away from the aperture upon insertion of an endotracheal tube or other longitudinally-extended element inserted through the airway tube so as to emerge into the hollow or lumen of the mask through the mask aperture. Aspects of the present invention may for example be applied to single or re-useable devices, devices featuring aperture bars or not, "intubating" devices which permit an endotracheal tube or similar to be introduced into the larynx via an airway tube of a mask, devices incorporating fiberoptic viewing devices and so forth, without restriction or limitation on the scope of the present invention.

The invention claimed is:

1. An artificial airway device to facilitate lung ventilation of a patient, comprising an airway tube, a gastric drain tube and a mask at one end of the airway tube, the mask including a backplate and having a peripheral formation adapted to form a seal around the circumference of the laryngeal inlet when the device is in situ, the peripheral formation surrounding a hollow interior space in the form of a lumen of the mask and the airway tube opening into the lumen of the mask, wherein the mask includes an atrium for passage to the drain tube of gastric matter leaving the oesophagus when the device is in situ, wherein the atrium is defined by a wall of the backplate, wherein the wall comprises an outer skin and an inner skin, the outer skin comprising part of the gastric drain tube, the inner skin comprising a part of the airway tube.

2. A device according to claim 1, wherein the atrium is formed between the inner and outer skins.

3. A device according to claim 1, the inner skin including an inlet to the atrium.

4. A device according to claim 1, wherein the inner and outer skins are formed from a resiliently deformable material that is softer in durometer than the material of the airway tube.

5. A device according to claim 1, wherein the airway tube is disposed within the gastric drain tube.

6. A device according to claim 5, the part of the gastric drain tube being an integrally formed part thereof.

7. A device according to claim 5, the said part of the airway tube comprising a bore in fluid communication with the lumen of the mask.

8. A device according to claim 5, wherein the gastric drain tube has an interior space and wherein the airway tube establishes a separation of the interior space within the gastric drain tube into two gastric conduits.

9. A device according to claim 5, wherein the gastric drain tube comprises an expansible material.

10. A device according to claim 1, wherein the backplate wall outer skin comprises a transparent or translucent material to allow for a visual inspection of the device's contents when the device is removed from the patient.

11. A device according to claim 10, wherein the outer skin comprises a transparent material.

* * * * *